(12) United States Patent
Lee

(10) Patent No.: US 10,183,114 B2
(45) Date of Patent: Jan. 22, 2019

(54) METHOD AND APPARATUS FOR AUTOMATICALLY ADJUSTING INJECTION RATE THROUGH FALLING

(71) Applicant: ACE MEDICAL CO., LTD., Goyang-si, Gyeonggi-do (KR)

(72) Inventor: Jong-Woo Lee, Seoul (KR)

(73) Assignee: ACE MEDICAL CO., LTD., Goyang-si (KR)

( * ) Notice: Subject to any disclaimer, the term of this patent is extended or adjusted under 35 U.S.C. 154(b) by 712 days.

(21) Appl. No.: 14/685,004

(22) Filed: Apr. 13, 2015

(65) Prior Publication Data
US 2015/0224256 A1   Aug. 13, 2015

Related U.S. Application Data

(63) Continuation of application No. PCT/KR2013/009139, filed on Oct. 14, 2013.

(30) Foreign Application Priority Data

Oct. 15, 2012  (KR) .................... 10-2012-0114451
Nov. 2, 2012   (KR) .................... 10-2012-0123805
Oct. 1, 2013   (KR) .................... 10-2013-0117441

(51) Int. Cl.
    *A61M 5/14*   (2006.01)
    *A61M 5/168*  (2006.01)
    *A61M 5/172*  (2006.01)

(52) U.S. Cl.
    CPC ...... *A61M 5/16813* (2013.01); *A61M 5/1411* (2013.01); *A61M 5/1415* (2013.01); *A61M 5/1689* (2013.01)

(58) Field of Classification Search
    CPC .......... A61M 5/16813; A61M 5/16818; A61M 5/1689; A61M 5/1415; A61M 5/1417
    See application file for complete search history.

(56) References Cited

U.S. PATENT DOCUMENTS 4,105,028 A * 8/1978 Sadlier ............... A61M 5/1689
                                              128/DIG. 13
4,137,940 A * 2/1979 Faisandier .......... A61M 5/1689
                                              137/486

(Continued)

FOREIGN PATENT DOCUMENTS

JP   08-191891 A     7/1996
JP   2011-206082 A  10/2011

(Continued)

*Primary Examiner* — Bradley J Osinski
*Assistant Examiner* — William Frehe
(74) *Attorney, Agent, or Firm* — Jefferson IP Law, LLP

(57) ABSTRACT

The present invention relates to an apparatus and a system for controlling an amount of medicine or fluid injection through falling due to potential energy of the fluid. For example, the present invention can automatically adjust an injection rate of a medicine injected into a patient by controlling an opening/closing degree of a medicine hose by using a driving element driven by electric power according to a comparison of the number of drops with a predetermined value. An apparatus for realizing the method includes an accommodating case for accommodating a connecting portion for connecting a fluid, a detection unit for detecting the number of drops, a control unit for comparing the information detected by the detection unit, and a driving element for opening and closing a passage of the medicine hose based on the contents analyzed by a control unit.

11 Claims, 23 Drawing Sheets

(56) References Cited

U.S. PATENT DOCUMENTS

| | | | | |
|---|---|---|---|---|
| 4,652,262 A | * | 3/1987 | Veracchi | A61M 5/1689 128/DIG. 13 |
| 5,221,268 A | * | 6/1993 | Barton | A61M 5/16813 251/7 |
| 5,439,442 A | * | 8/1995 | Bellifemine | A61M 5/1689 604/65 |
| 6,491,659 B1 | * | 12/2002 | Miyamoto | A61M 5/1689 604/30 |
| 2005/0027237 A1 | * | 2/2005 | Weiner | A61B 5/021 604/66 |
| 2005/0059926 A1 | * | 3/2005 | Sage, Jr. | A61M 5/168 604/65 |
| 2009/0227939 A1 | * | 9/2009 | Mernoe | A61M 5/1413 604/65 |
| 2011/0282277 A1 | | 11/2011 | Kim | |
| 2013/0211323 A1 | * | 8/2013 | Lee | A61M 5/14228 604/67 |

FOREIGN PATENT DOCUMENTS

| KR | 10-0239937 B1 | 1/2000 |
|---|---|---|
| KR | 10-2005-0014908 A | 2/2005 |
| KR | 10-0643086 B1 | 10/2006 |
| KR | 10-2012-0076604 A | 7/2012 |

* cited by examiner

[Fig. 1]
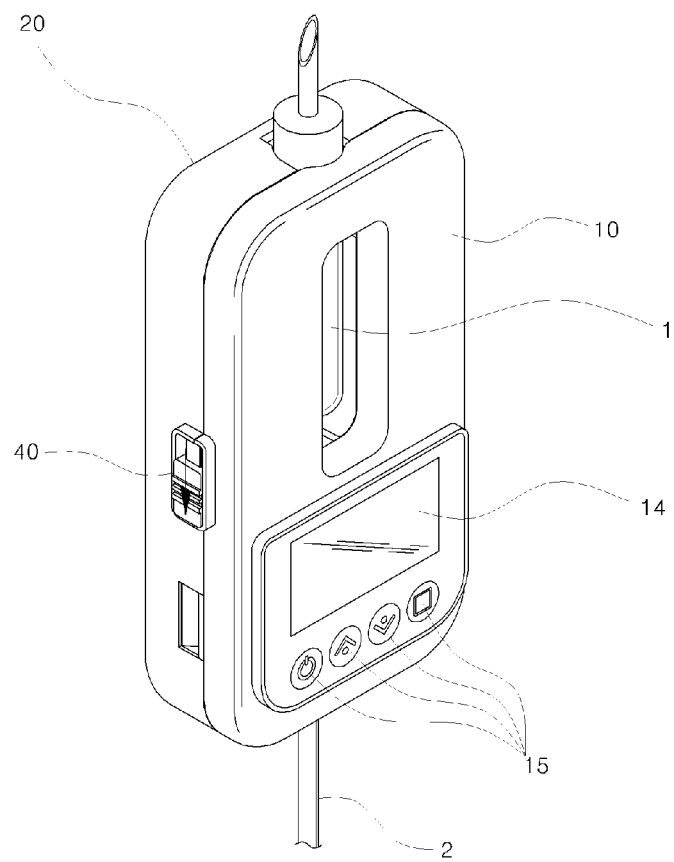

[Fig. 2]
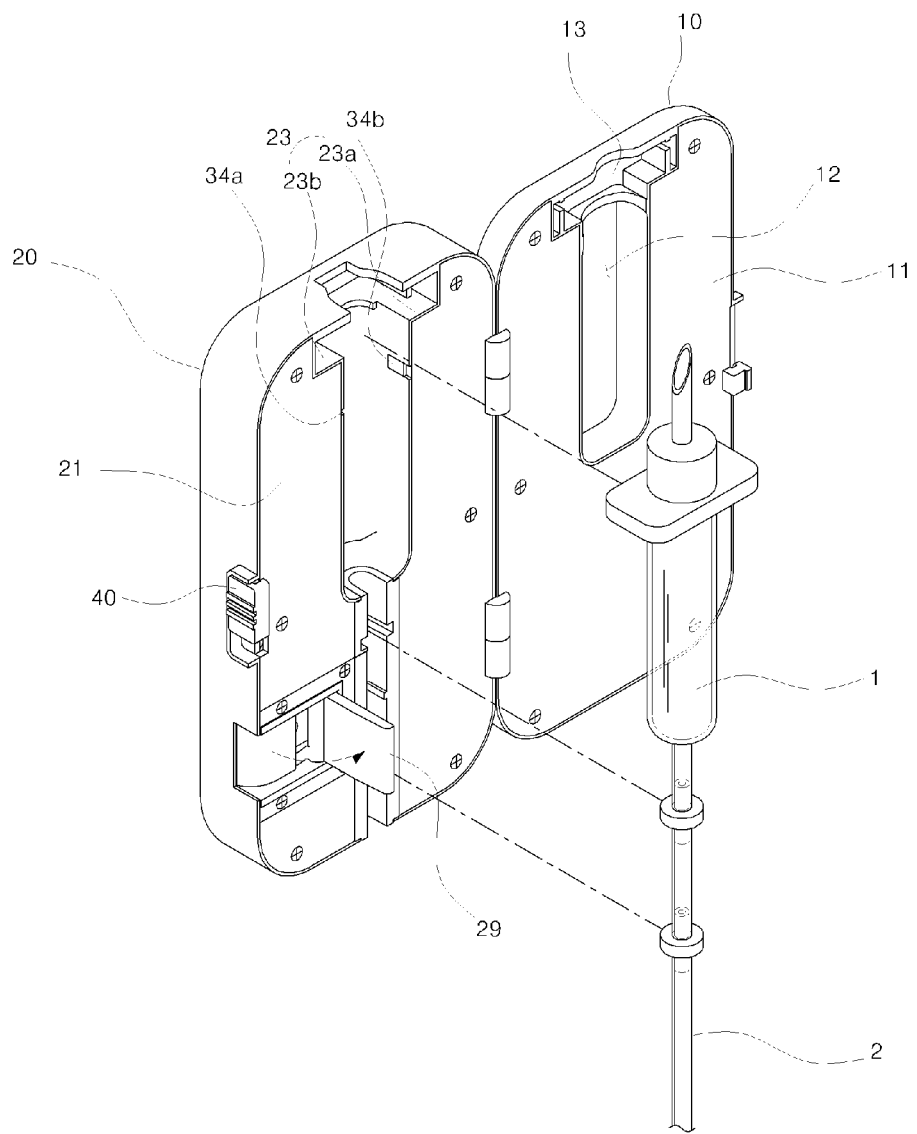

[Fig. 3]
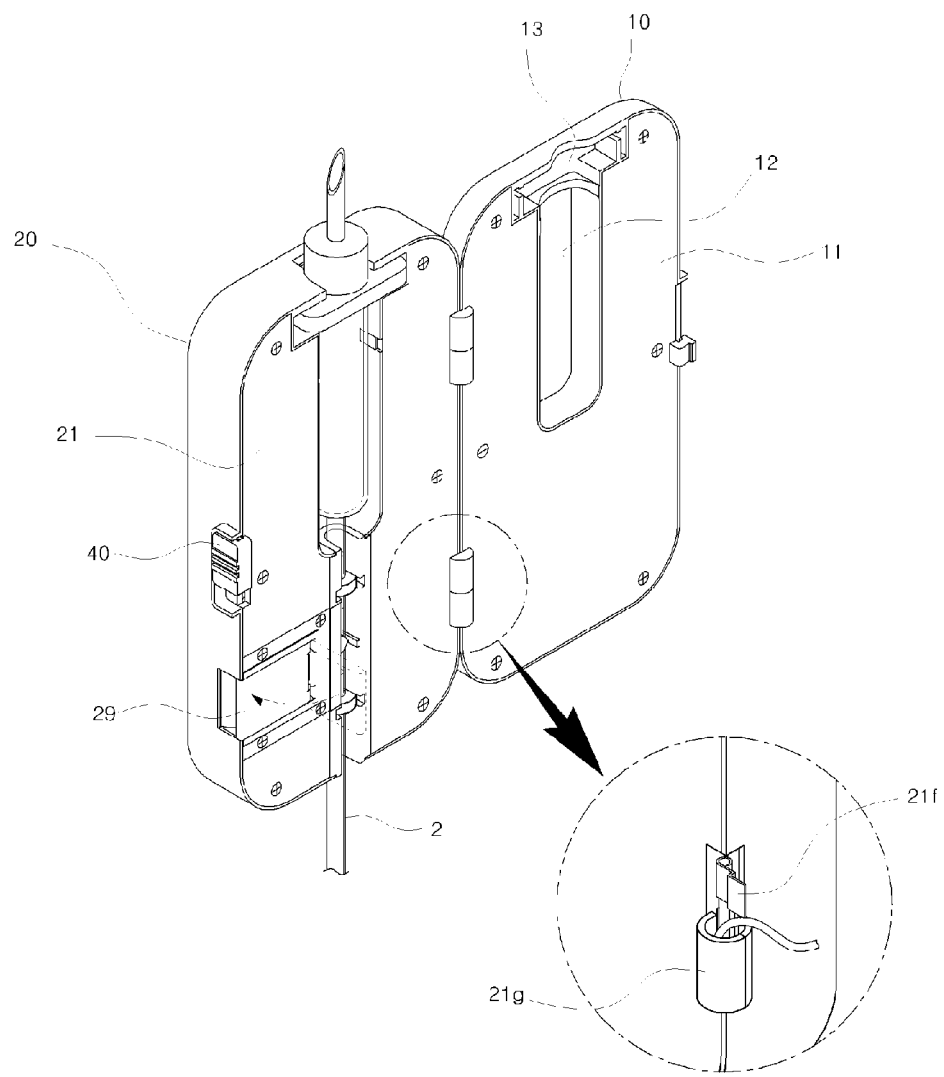

[Fig. 4]
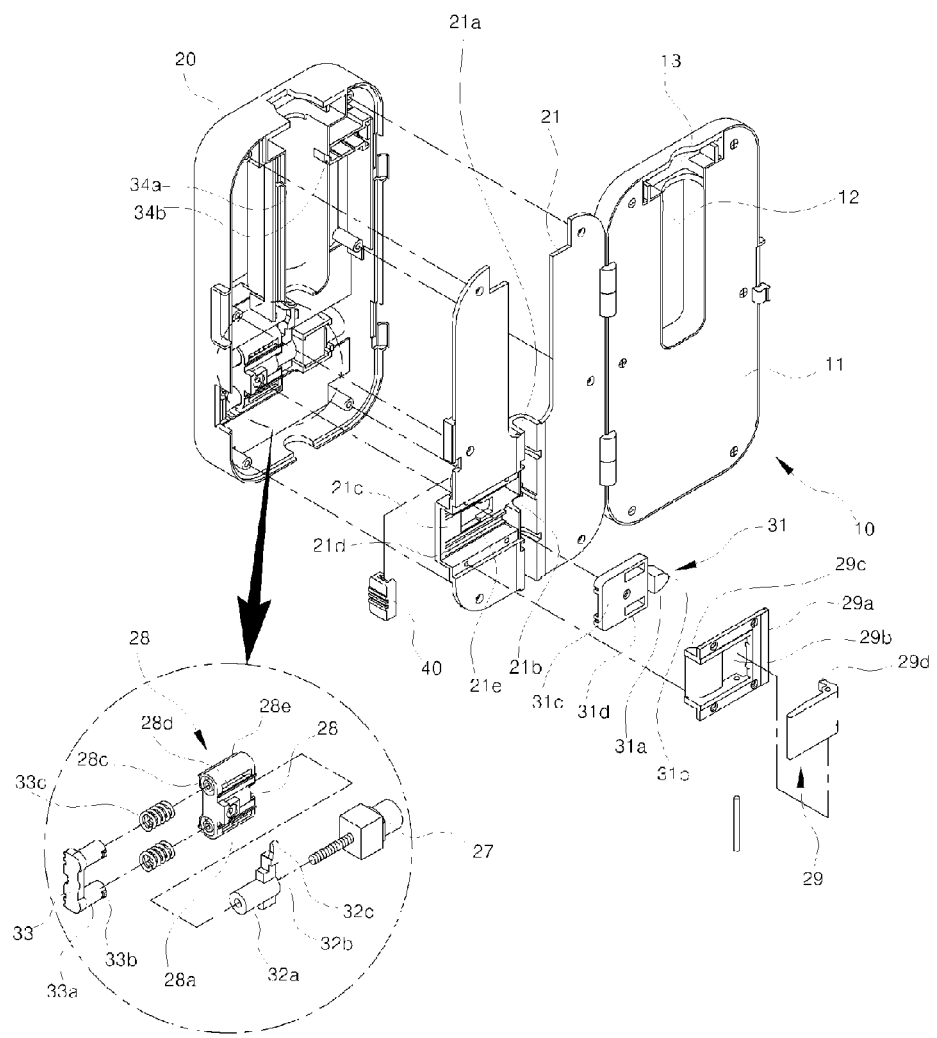

[Fig. 4a]
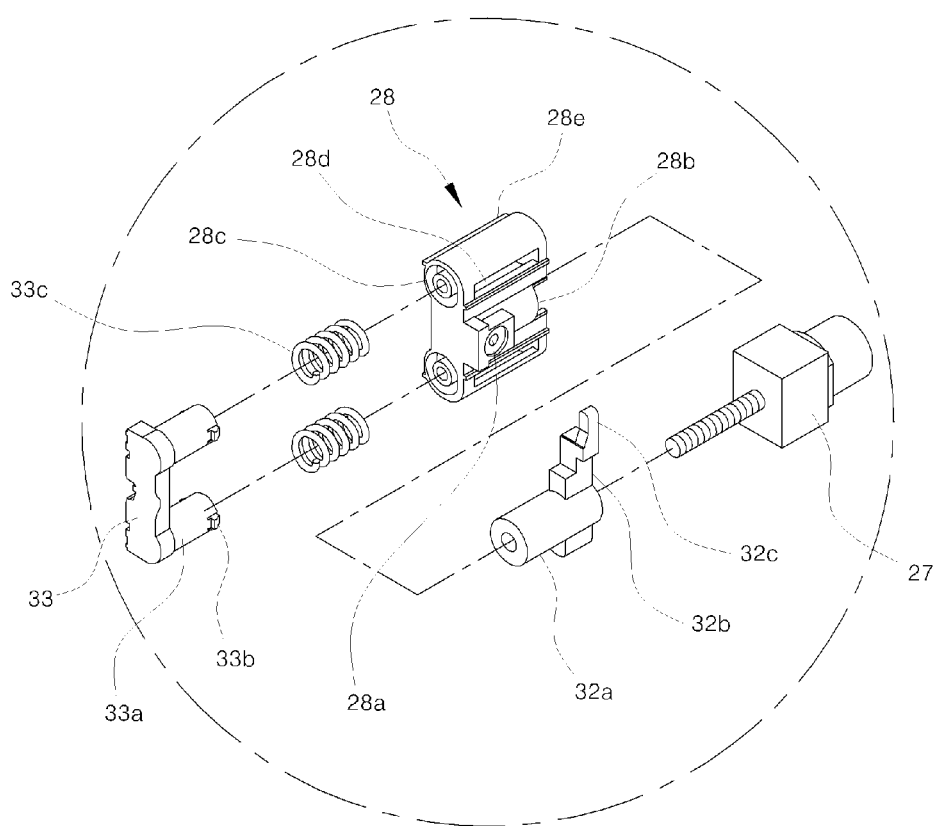

[Fig. 5]
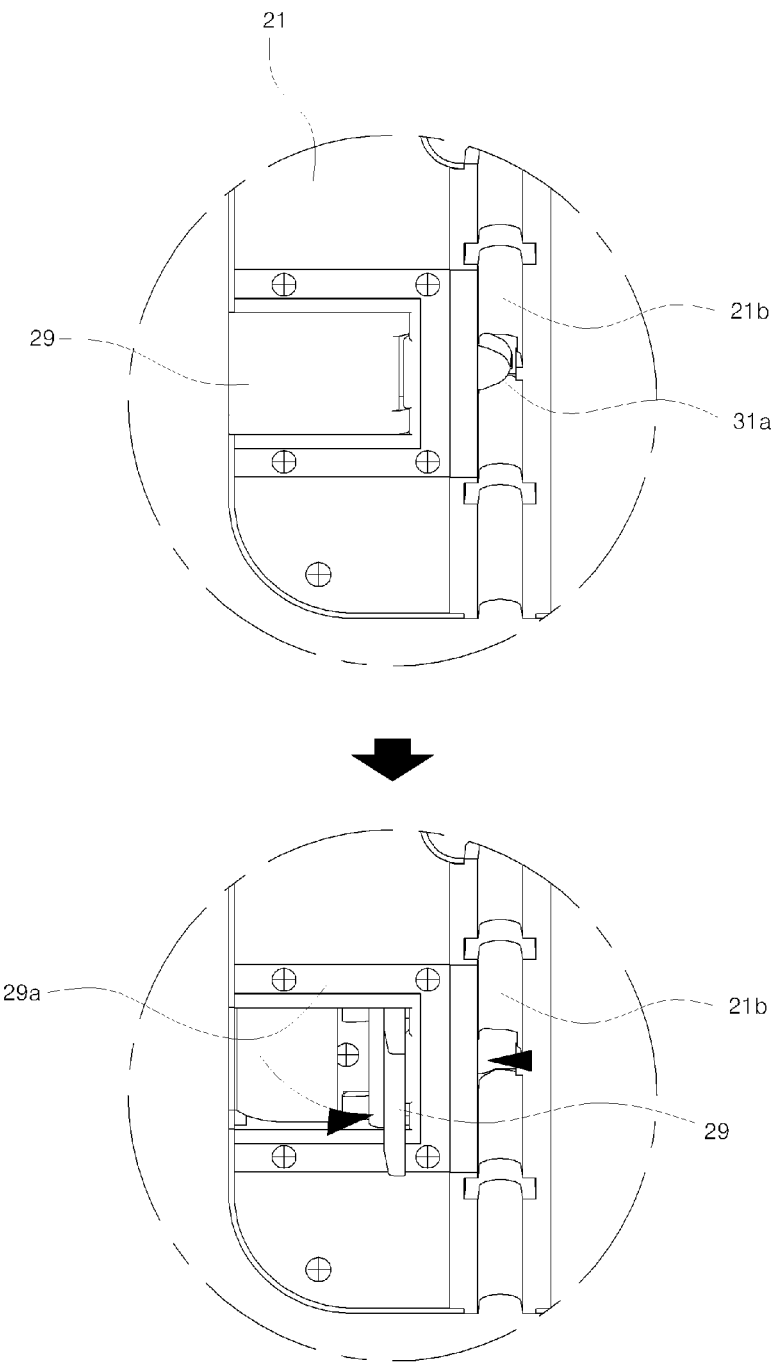

[Fig. 6]
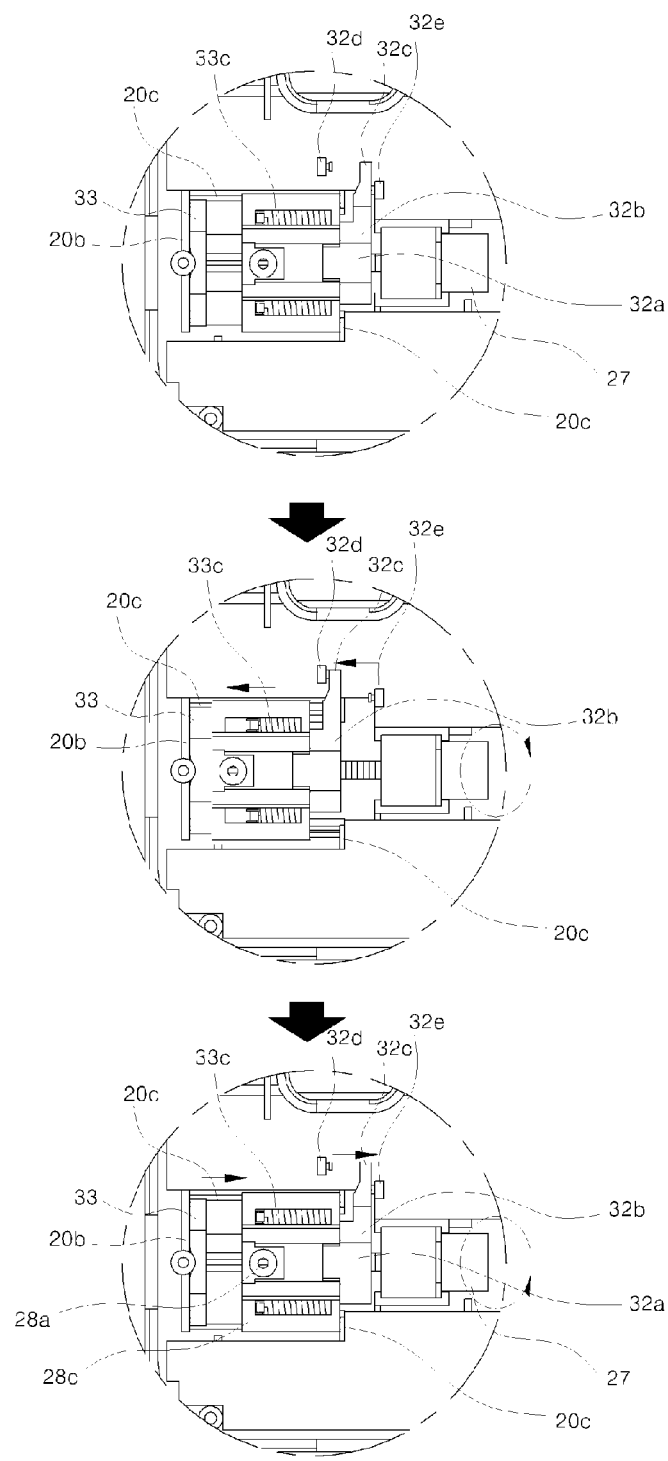

[Fig. 7]
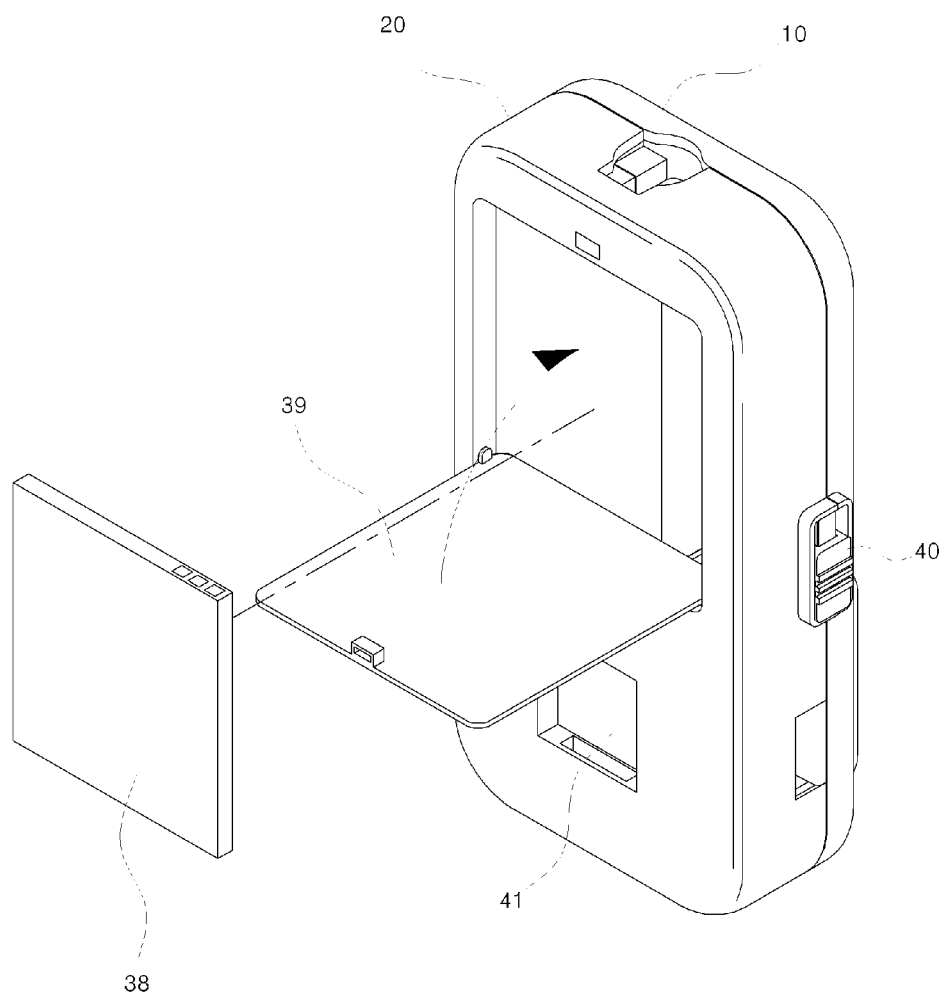

[Fig. 8]
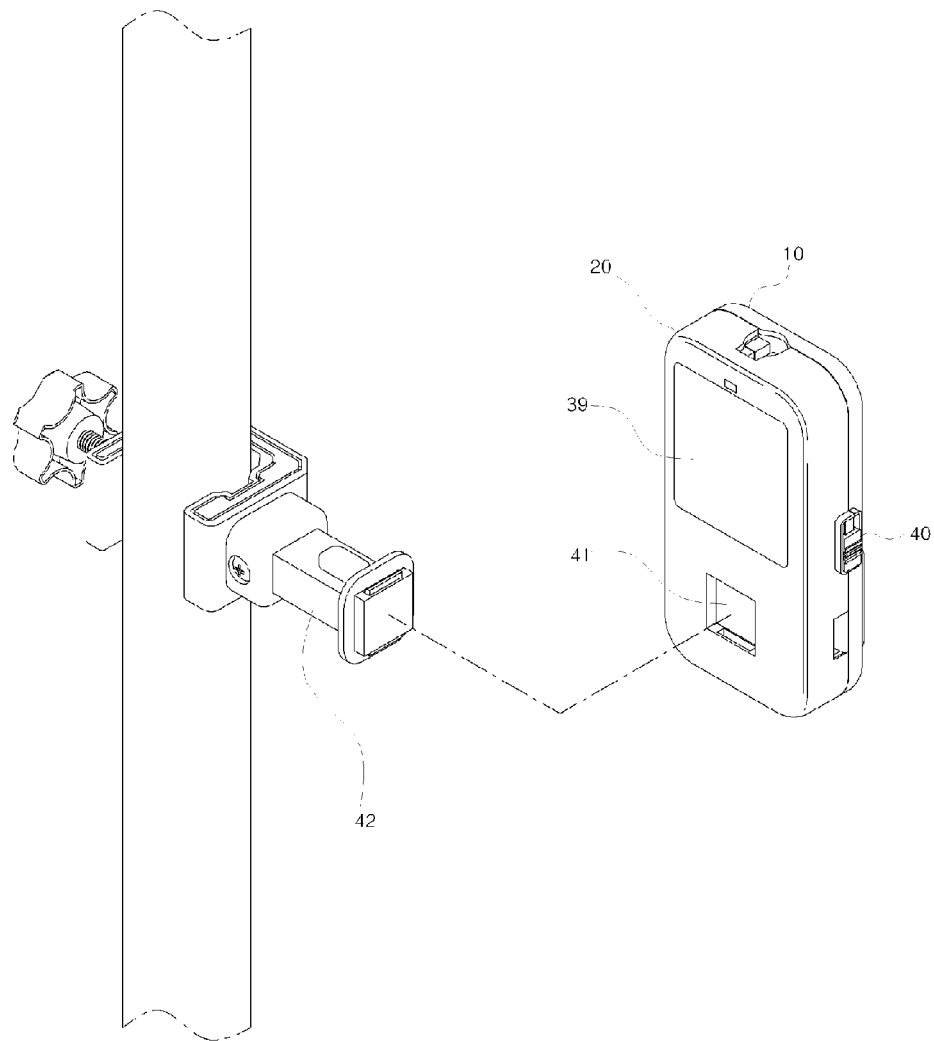

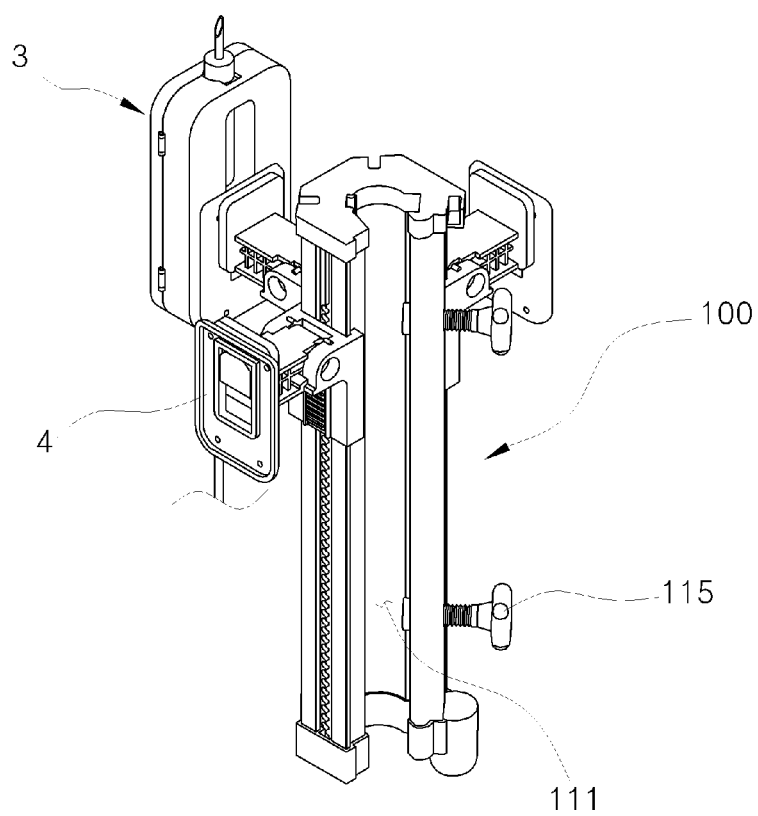
[Fig. 9]

[Fig. 10]
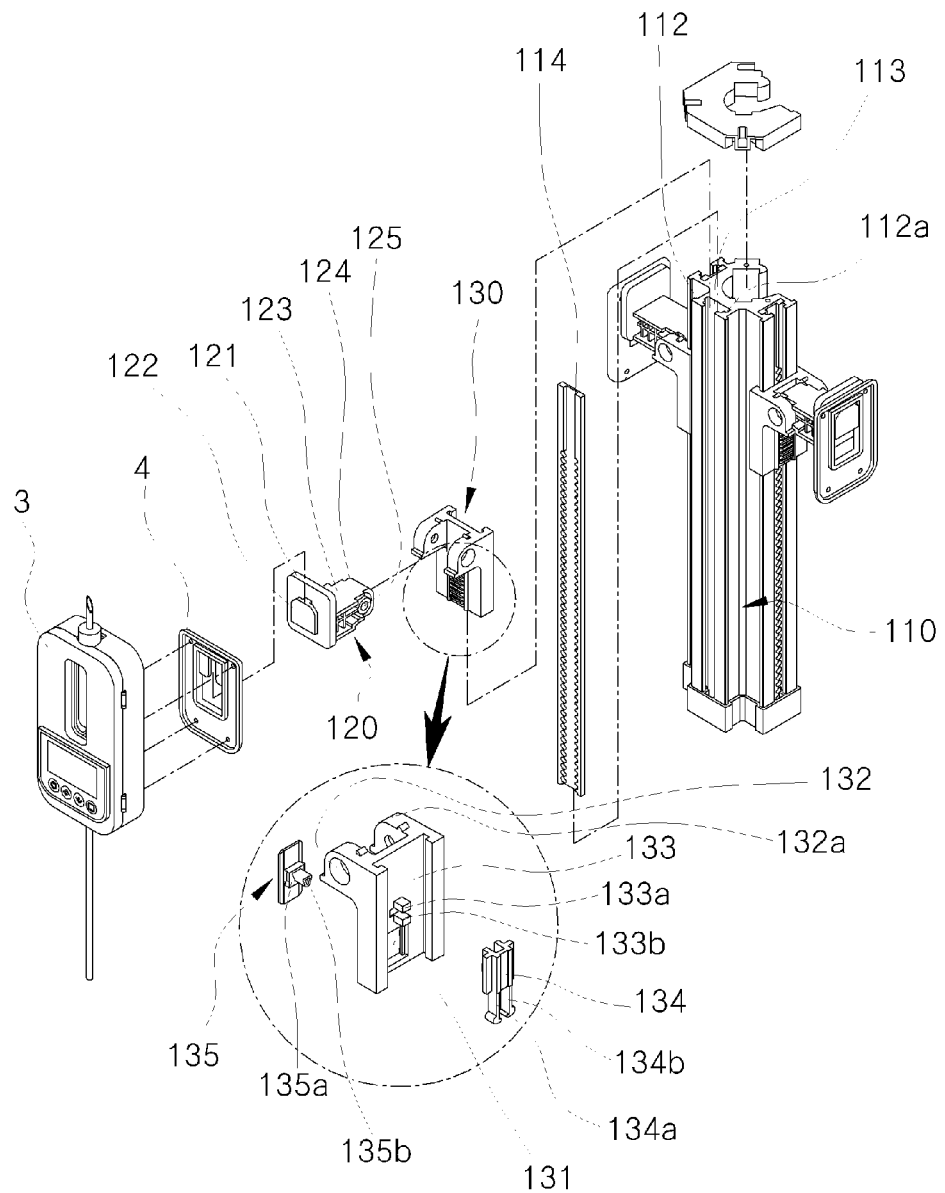

[Fig. 11]
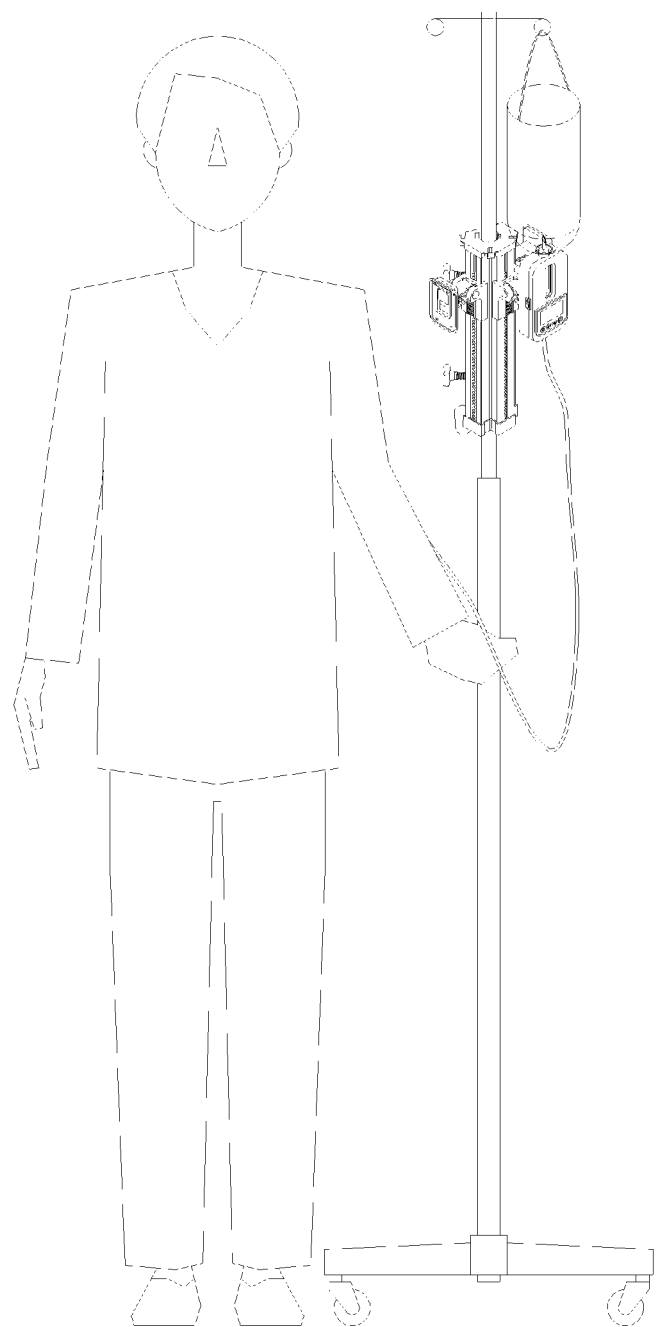

[Fig. 12]
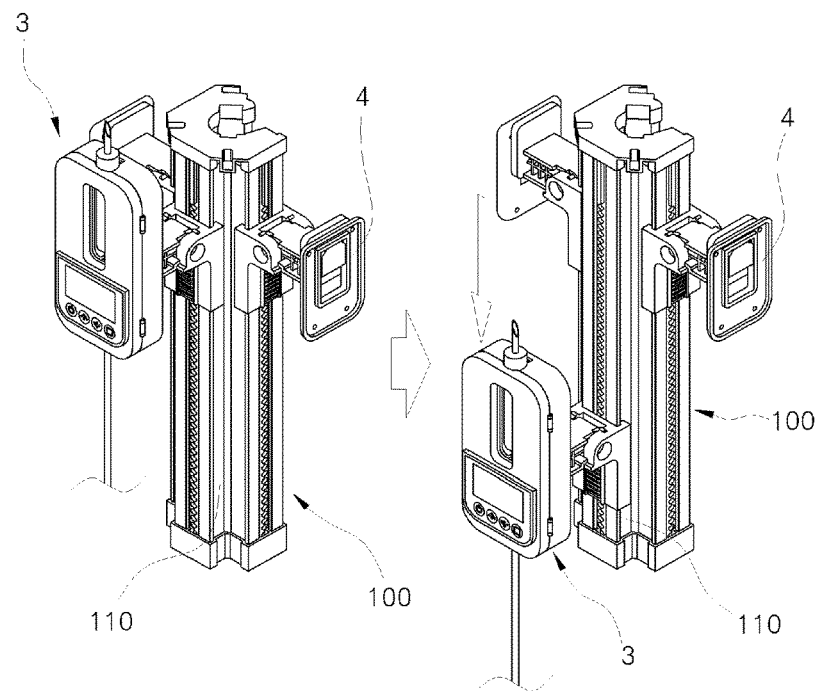
[Fig. 12a]
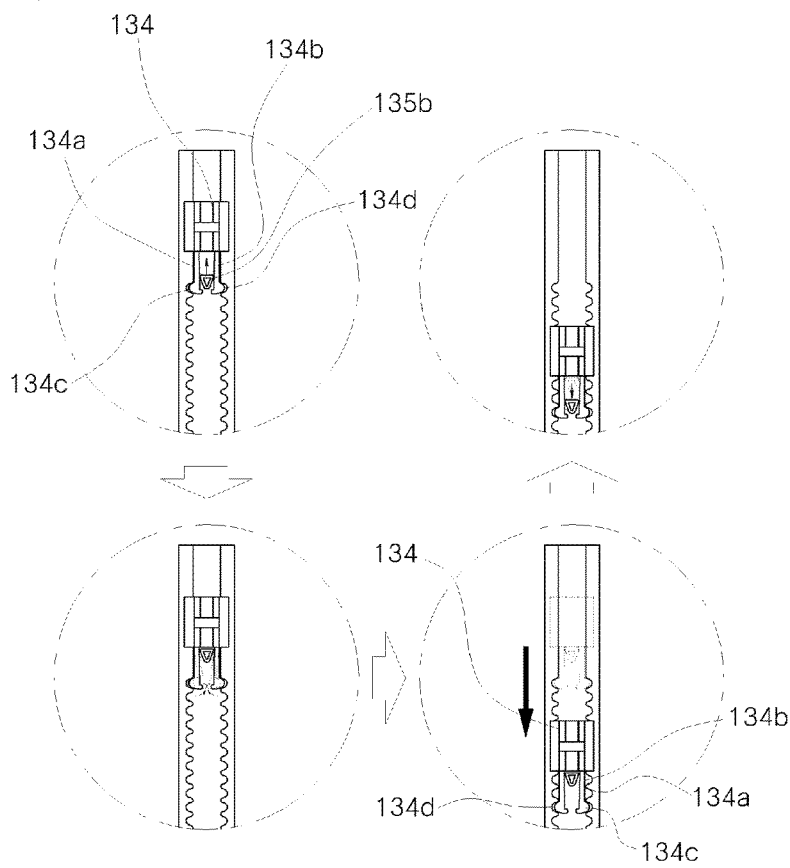

METHOD AND APPARATUS FOR AUTOMATICALLY ADJUSTING INJECTION RATE THROUGH FALLING

CROSS-REFERENCE TO RELATED APPLICATION(S)

This application is a continuation application of International Application No. PCT/KR2013/009139, filed Oct. 14, 2013, which claims the benefit under 35 U.S.C § 365 of a Korean patent application filed on Oct. 15, 2012 in the Korean Intellectual Property Office and assigned Serial number 10-2012-0114451, and of a Korean patent application filed on Nov. 2, 2012 in the Korean Intellectual Property Office and assigned Serial number 10-2012-0123805, and of a Korean patent application filed on Oct. 1, 2013 in the Korean Intellectual Property Office and assigned Serial number 10-2013-0117441, the entire disclosure of each of which is hereby incorporated by reference

TECHNICAL FIELD

The present invention relates to a method of automatically adjusting an injection through falling which is capable of improving a scheme of injecting fluid through falling by potential energy when the fluid (that is called Ringer's injection) is injected into a long or short-period hospitalized patient, and an apparatus for the same.

More particularly, the present invention relates to a method of automatically adjusting an injection through falling which is capable of automatically controlling a quantity of fluid injected through free fall to allow the fluid to be uniformly injected and in addition, of controlling the injection such that a suitable quantity of fluid is injected even when a plurality of fluid packs is used, and an apparatus for the same.

BACKGROUND ART

Currently, since a free-falling scheme is almost used when fluid is injected into a hospitalized patient, a nurse must frequently adjust the number of fluid drops which is varied with time after number of fluid drops is adjusted.

Conventionally, since the quantity of one drop is constant, it is possible to inject the exact quality of fluid through the dropping times of the fluid, so that this injection scheme has been used in hospitals until now.

As well known in the art, when the number of falls is 20 times, the quantity is 1 d. Thus, the injection quantity of 200 ml may be injected during two hours by suitably adjusting the number of falls.

However, the number of falls is dependent on a falling speed and the falling speed is generally dependent on the volume of a fluid pack or a hydraulic pressure varied with a position on which the fluid pack hangs, so a nurse generally adjusts the injected fluid by controlling an opening state of a medical fluid hose by using a clamp of a roller type installed to the medical fluid hose for injection (Korea Patent Patent No. 10-0813381).

However, when using the clamp, as the quantity of fluid reserved in the fluid pack is gradually reduced, the hydraulic pressure is reduced so that the number of falling is slow. Specifically, together with the above problem, if a nurse does not suitably adjust the quantity of fall for a suitable time period when an accurate injection of medical fluid is required, it is failed to suitably inject a quantity of medical fluid into a patient according to the prescription of a doctor so that a serious problem may be caused.

Thus, in recent, although an automatic injection apparatus capable of controlling a quantity of fluid has be developed and used, the automatic injection apparatus is very expensive since the automatic injection apparatus includes an injector and a controller as a set. In addition, in the state that the injection quantity is settled, the quantity of fluid may be changed according to the power current, so that it is difficult to achieve sufficient effect (Korean Patent No. 10-0530848, Korean Unexamined Patent Publication No. 10-2010-0027806).

Further, since the injection is performed to many patients in a hospital and the control of injection quantity is only dependent on nurse's personal exertions, it is very hard and difficult for the nurses caring many patients to adjust always and precisely the injection quantity.

DISCLOSURE

Technical Problem

Accordingly, it is an object of the present invention to provide a clamp for automatically adjusting injection rate precisely while employing a falling method, and thus to solve a problem of the related art by interrupting the clamp at one site even when a plurality of clamps are used.

Technical Solution

To achieve this, the present invention can automatically adjust an injection rate of a medicine injected into a patient by controlling an opening/closing degree of a medicine hose by using a driving element driven by electric power according to a comparison of the number of drops with a predetermined value.

The apparatus for realizing the method includes an accommodating case for accommodating a connecting portion for connecting a fluid, a detection unit for detecting the number of drops, a control unit for comparing the information detected by the detection unit, and a driving element for opening and closing a passage of the medicine hose based on the contents analyzed by a control unit.

In the apparatus, operation information of a device is transmitted through a communication unit to a main server by a serial number individually given to the device, the information transmitted can be displayed by a main server so that nurses can identify the information, the main server transmits information requesting a change to the device, and a control unit controls the driving elements based on the information to change injection rate so that a plurality of devices can be interrupted at one site.

Advantageous Effects

Thus, according to the present invention, even when a fluid is injected through falling due to potential energy, the fluid is automatically controlled so that the fluid can be uniformly supplied to a patient. (For reference, the dropping fluid is not limited to water and may include a fluid pack hung on a linger and various types of medicines according to a medicine bottle.

Further, since the automatic clamp can be attached to or detached from the medicine hose, a complex connection is not necessary, and in particular, in the case of hoses having different diameters, various types of medicine hoses can be used regardless of the diameters of the hoses.

In addition, the present invention can install a plurality of automatic clamps at one site by using a fixing unit and a management server, and in particular, can manage the automatic clamps at one site.

DESCRIPTION OF DRAWINGS

FIG. 1 is a perspective view of an automatic clamp according to an embodiment of the present invention.

FIG. 2 is a perspective view of an automatic clamp according to the embodiment of the present invention.

FIG. 3 is a perspective view of an automatic clamp according to the embodiment of the present invention.

FIG. 4 is an exploded perspective view of an automatic clamp according to the embodiment of the present invention.

FIG. 4A is an enlarged view of a movable member embedded in the automatic clamp according to the embodiment of the present invention.

FIG. 5 is a view showing an operation state of an attaching/detaching lever installed in a side surface of the automatic clamp according to the embodiment of the present invention.

FIG. 6 is a view showing an operation state of a movable member embedded in the automatic clamp according to the embodiment of the present invention.

FIG. 7 is a rear perspective view of the automatic clamp according to the embodiment of the present invention.

FIG. 8 is a rear perspective view showing that a fixing arm is installed in a docking part according to the embodiment of the present invention.

FIG. 9 is a perspective view of a fixing apparatus and the automatic clamp according to the embodiment of the present invention.

FIG. 10 is an exploded perspective view of the fixing apparatus and the automatic clamp according to the embodiment of the present invention.

FIG. 11 is a view showing an in-use state of the fixing apparatus and the automatic clamp according to the embodiment of the present invention.

FIGS. 12 and 12a are views showing an operation state of the fixing apparatus and the automatic clamp according to the embodiment of the present invention.

BEST MODE

Mode for Invention

Figure 13:
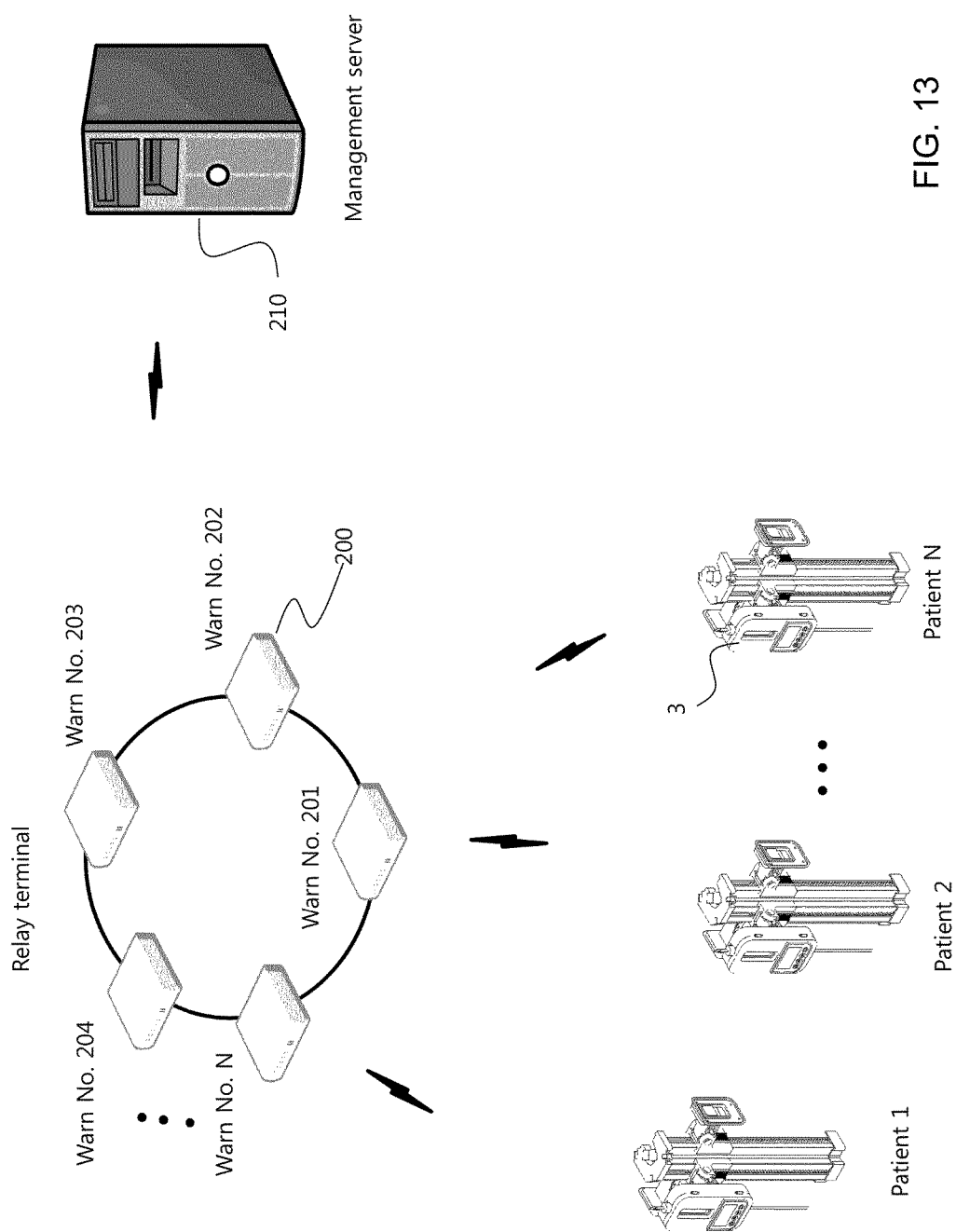
FIG. 13 is an exemplary view of a system according to the embodiment of the present invention.

The present invention relates to an apparatus for adjusting injection rate through falling, wherein a first box 10 having a first accommodating part 12 extending from one side toward an opposite side thereof and a second box 20 having a second accommodating part 22 extending together with the first accommodating part 22 to accommodate a chamber are hinge-coupled to each other such that one side surface of the first box 10 and one side surface of the second box 20 face each other when the first box 10 and the second box 20 are folded, an inwardly curved gully into which a hose is inserted when a chamber is accommodated is formed on one of the side surfaces of the first box 10 and the second box 20, a driving unit 30 controls a speed of a medicine dropping into the chamber by pressing an outer circumference of a hose 2 inserted into the gully, a detection unit 34 detects a movement of a medicine dropping into the chamber 1 accommodated in the first accommodating part 12 and the second accommodating part 22, a control unit 35 controls a speed of a dropping medicine by controlling the driving unit when a button is manipulated or from the fact detected by the detection unit and displays and guides the fact identified through a display panel formed at one side thereof, and a locking unit 40 fixes the first box 10 and the second box 20 such that one side surface 11 of the first box 10 and one side surface 21 of the second box 20 are attached to each other when the first box 10 and the second box 20 are folded.

Hereinafter, detailed contents for carrying the present invention will be described in detail with reference to the accompanying drawings.

FIG. 1 is a perspective view showing an entire appearance of an automatic clamp according to an embodiment of the present invention. FIGS. 2 and 3 show states before and after a chamber 1 of a fluid pack is accommodated while the automatic clamp of FIG. 1 is unfolded. FIG. 4 shows an in-use state of the automatic clamp according to the embodiment of the present invention.

As shown in the drawings, according to the embodiment of the present invention, a first box 10 having a first accommodating part 12 extending from one side toward an opposite side thereof and a second box 20 having a second accommodating part 22 extending together with the first accommodating part 12 to accommodate a chamber are hinge-coupled to each other such that one side surface of the first box 10 and one side surface of the second box 20 face each other when the first box 10 and the second box 20 are folded.

A gully is formed on one side surface of the first box 10 or the second box 20, a driving unit 30 controls a speed of a medicine dropping into the chamber by pressing an outer circumference of a hose 2 inserted into the gully, a detection unit 34 detects a movement of a dropping medicine of the chamber 1 accommodated in the first accommodating part 12 and the second accommodating part 22, a control unit 35 controls a speed of a dropping medicine by controlling the driving unit when a button is manipulated or from the fact detected by the detection unit and displays and guides the fact identified through a display panel formed at one side thereof, and a locking unit 40 fixes the first box 10 and the second box 20 such that one side surface 11 of the first box 10 and one side surface 21 of the second box 20 are attached to each other when the first box 10 and the second box 20 are folded.

A cutaway recess 34a is formed on an outer wall of one of the first accommodating part 12 and the second accommodating part 22 and another cutaway recess 34b are formed on an outer wall of the other of the first accommodating part 12 and the second accommodating part 22, such that an embedded sensor 34c crosses the cutaway recesses 34a and 34b and the detection unit 34 detects a movement of the medicine dropping into the chamber when the chamber is accommodated in the recesses 34a and 34b.

A first connecting part 13 and a second connecting part 23 extending from the first accommodating part 12 and the second accommodating part 22 to enclose an upper portion of the chamber are formed at upper portions of the first box and the second box. The first connecting part 13 and the second connecting part 23 fix a support step 23a formed by extending upper ends of the side surfaces 11 and 21 of the first box and the second box to the outside and cutting away the extending upper ends of the side surfaces 11 and 21 such that an upper end of the chamber is laid on the support step 23a, and the chamber accommodated in the first accommodating part and the second accommodating part by forming a through-hole enclosing a periphery of an upper end of the chamber when the first and second boxes are folded.

For reference, a stopping step is formed in the first box 10 and a bent coupling piece 40a is formed in the second box 20, such that the locking unit 40 fixes the first box 10 and the second box 20 as the coupling piece is stopped by the stopping step 40b formed in the first box 10 when the coupling piece is slid upward and downward. The locking unit is not limited thereto, and may be variously modified according to embodiments.

A gully 21a extending from a lower end of the second accommodating part 22 to a lower end of the second box and curved inward is formed on one side surface 21 of the second box.

The driving unit 30 for determining an opening degree of the hose 2 of the chamber by pressing the hose 2 when the hose is inserted into the gulley is provided in the gulley 21a.

That is, as shown in FIGS. 4 to 7, the driving unit includes an attaching/detaching lever 29, a pressing member 31, a movable member 28, and a driving motor 27. An assembly plate to which the lever 29 is mounted and a positioning recess 21C in which the pressing member is positioned are formed on the side surface of the second box 20, and an inward hole 21b connecting the positioning recess 21C and the gulley 21a are formed such that a protrusion 31a of the pressing member 31 appears inside and outside the inward hole as the lever 29 is moved. The movable member 28 that is moved from one side to an opposite side according to an operation of the driving motor 27 is installed in the second box 20 within the positioning recess 21c, and the pressing member 31 located on an upper side of the cutaway space and the movable member 28 located on a lower side of the cutaway space are coupled to each other. As the pressing member 31 assembled with the movable member 28 is moved together with the movable member 28 as the driving motor 27 is moved, the hose is pressed to control an opening degree of the hose while the protrusion 31a appears inside and outside the inward hole 21b.

For reference, the attaching/detaching lever 29 is configured to move the pressing member 31 located inside the positioning recess while a protruding piece 29d formed at a lower end of the lever 29 appears inside and outside a cutaway portion 29c when the lever is coupled to be rotated, by forming a flat assembly plate 29a and forming a burying part 29b having the cutaway portion 29c at a lower portion of the assembly plate 29a.

The pressing member 31 has a flat guide plate 31c,a protrusion 31a formed at one end of the guide plate at a height larger than a thickness of the guide plate, a guide groove 31d that is cutaway transversely, and a coupling hole extending from an upper side to a lower side thereof, so that the protruding piece 29d of the lever 29 exposed to the outside of the cutaway space 29b is located inside the guide groove 31d.

Thus, if the attaching/detaching lever (hereinafter, also referred to as 'the lever') is pulled, the protruding piece 29d in the guide groove 31d moves downward while rotating to pull the pressing member 31 to the outside, in which case the pressing member 31 is pulled so that the protrusion 31a pressing the hose is moved to an inside of the inward hole 21b and the hose and the chamber in the gulley can be replaced.

Then, a protruding portion 31b protruding in a direction perpendicular to the hose 2 inserted into the gulley 21a is formed in the protrusion 31a, so that the outer surface of the hose 2 can be precisely pressed while a contact area of the protruding portion 31b is minimized.

A pair of guides 21d protruding leftward and rightward is formed in the positioning recess 21c to which the lever 29 and the pressing member 31 is mounted, and a space 21e that is cutaway leftward and rightward is formed between the adjacent two guides such that the pressing member 31 can be moved leftward and rightward along the guides 21d. In particular, the pressing member 31 is screw-coupled to the movable member 28 located below the cutaway space 21e while the cutaway space 21e is interposed between the movable member 28 and the pressing member 31 such that the pressing member 31 is moved together with the movable member 28 during an operation of the movable member 28.

That is, the movable member 28 includes a coupling part 28a located in the cutaway space 21e to connect the pressing member 31 and the movable member 28 when the pressing member 31 and the movable member 28 is connected to each other, a tubular accommodating pipe 28c formed at left and right sides of the coupling part and the accommodating hole 28b such that one side of the accommodating pipe 28c is blocked, a protruding pin formed inside the accommodating pipe 28c, and a cutting line 28d that is cutaway leftward and rightward on an outer side of the accommodating pipe 28c.

The support piece 33 in which a resilient member 33c is fitted with a boss 33a is inserted into the accommodating pipe 28c, in which case a step 33b located inside the cutting line 28d to prevent separation of the movable member is formed in the boss 33a and the support piece 33 is inserted into and assembled in the movable member 28.

A protruding movable portion 28e is formed at a lower end of the movable member 28, a pair of guide grooves 20a spaced apart from each other by a predetermined separation is formed inside the second box 20, and a guide fixing piece 20b and a guide stopping piece 20c erected high are formed at opposite ends of the guide groove, so that the movable member 28 can be moved forward and rearward along the guide groove 20a.

A stopper 32 that reports an opened state of the medicine hose while linearly reciprocating along a screw thread to a rotary shaft is coupled to the driving motor 27 that moves the movable member 28.

A pair of wings 32b are formed on left and right side surfaces of a circular column of the stopper 32 and a protruding stopping piece 32c is formed in one of the wings, so that if the circular column 32a fitted with the rotary shaft of the driving motor 27 is inserted into the accommodating hole 28b of the movable member with a certain clearance, the wings 32b formed on the left and right side surfaces of the circular column 32a are located at a rear end of the accommodating pipe 28c of the movable member 28 to push the movable member 28 to the outside.

Then, the stopping pieces 32c of the wings 32b are located between a pair of limit switches 32d and 32e installed in a control board to limit a movement of the column 32 within a predetermined range, and enables the limit switches 32d and 32e to report an opened state of the hose when the limit switches 32d and 32e are touched.

That is, if it is instructed that an amount of medicine is increased, the driving motor 27 is rotated, in which case the stopper 32 fitted with the rotary shaft of the driving motor 27 is moved along a screw thread of the rotary shaft to gradually push the movable member 28 located at a tip end of the stopper 32.

Then, the resilient member 33c located within the accommodating pipe 28c of the movable member 28 is contracted, and if the driving motor 27 continues to be rotated, the stopping piece 32c of the stopper 32 touches one limit switch 32d to inform the control unit that the hose is fully opened.

To the contrary, if it is instructed that an amount of medicine is decreased, the driving motor 27 is rotated reversely, in which case the stopper 32 fitted to the rotary shaft of the driving motor 27 is moved along a screw thread of the rotary shaft to gradually make a distance between the driving motor 27 and the stopper 32 closer.

Then, the movable member 28 located at a tip end of the stopper 32 is moved toward the driving motor 27 as the resilient member 33c contracted within the accommodating pipe 28a is expanded, in which case if the driving motor 27 continues to be rotated, the stopping piece 32c of the stopper 32 touches the other limit switch 32e to inform the control unit that the hose is closed.

Thus, according to the embodiment of the present invention, if the side surfaces 11 and 21 of the first box 10 and the second box 20 are attached to each other by folding the first box 10 and the second box 20 with respect to the chamber, a lower end of the chamber is located within the first accommodating part and the second accommodating part while the support step 23a and the through-hole 23b enclose an upper end of the chamber, in which case if the detection unit formed within the first accommodating part or the second accommodating part detects a movement of a medicine dropping into the chamber across the cutaway recess and informs the control unit of the fact, the control unit controls an opening degree of the hose by controlling the driving unit and moving the protrusion of the pressing member inserted into the gully, thereby adjusting an amount of the medicine supplied through falling.

As shown in FIG. 8, a space that is inwardly recessed by cutting away a portion of a rear end of the second box is formed at the rear end of the second box, and an opened space of the second box is blocked by a cover 39 after a rechargeable battery is inserted into the recessed space. Then, the cover 39 may be separated from the second box, but may be coupled to a rear end of the box to rotate the cover 39.

Then, the docking part 41 is formed at a rear end of the second box, and a fixing device or a fixing arm 42 may be connected to the rear end of the second box.

For reference, the docking part 41 is assembled by forming an inwardly recessed space and a stopping step at a rear end of the second box and inserting the fixing device into the inward space, but the docking part 41 having a separate inward space and a stopping step may be assembled according to an embodiment.

Hereinafter, in a detailed description with reference to FIGS. 9 to 11, the fixing device 100 is adapted to adjust a vertical location of the automatic clamp, and secures higher potential energy and support installation of a plurality of automatic clamps.

The fixing device 100 includes a gripping member 110 attached to a rod of a linger member, a hanger 120 on which the second box is hung to be fixed, and a connecting member 130 connecting the hanger and the gripping member.

In particular, the connecting member 130 is fitted with an outside of the gripping member to be moved upward and downward, so that a vertical height of the hanger connected to one side of the connecting member 130 can be adjusted.

For reference, an inwardly curved recess 111 is vertically formed in the gripping member 110, a pair of stopping steps 112 and 112a that are spaced apart from each other leftward and rightward are formed on the outside of the gripping member 110, and an inwardly recessed sliding groove 113 is formed between the two stopping steps.

A coupling member 114 is fixedly inserted into the sliding groove 113, and in particular, the coupling member is configured such that a plurality of screw threads face each other on the left and right sides of the inward space formed vertically.

Since a fixing screw 115 is coupled to an outside of the gripping part 110, and when a rod of the linger member is inserted into the inward recess, the fixing screw is fastened and fixed through screw-coupling.

An erected stopping piece 121 and a protruding stopper 122 are formed on the front side of a body 123 formed at a center of the hanger 120, and a coupling part 124 connected to the body and a rear end of which is curved is formed on the rear side of the body 123.

A coupling recess 125 or a coupling hole shaft-coupled to a connecting member is formed in the coupling part 124, which can be rotated upward and downward within a predetermined angle range.

A pair of coupling pieces 132 and 132a protruding on one side of an inward hole 131 that is cut away vertically is formed in the connecting member 130 coupled to the hanger, and a guide 133 enclosing the sliding groove 113 and outer surfaces of the stopping steps 112 and 112a are formed on an opposite side thereof.

The coupling part 124 of the hanger 120 is introduced into a space between the two coupling pieces 132 and 132a to be shaft-coupled, and the guide 133 is fitted with an outer side of the gripping member 110 to be moved upward and downward along the stopping steps 112 and 112a.

A pair of fixing bosses 133a and 133b protrudes upward and downward from an inside of the guide 133 of the connecting member, and a movable piece 134 is fixedly inserted between the two fixing bosses 133a and 133b.

A pair of resilient support pieces 134a and 134b having the same shape are erected while forming separated spaces on the left and right sides of the movable piece 134, and bosses 134c and 134d are formed at an end of the resilient support piece.

The movable piece 134 is located within the slide groove 113 of the gripping member 110 while the connecting member 130 is coupled in a sliding manner, and in particular, the resilient support pieces 134a and 134b are engaged with the screw thread of the coupling member 114 while being expanded and shrunk.

A fixing member 135 having a protrusion 135a is coupled to a front surface of the connecting member 130 to be inserted into the inward hole 131 and moved upward and downward, and in particular, a movable boss 135b passing through the inward hole 131 is formed on a rear surface of the fixing member 135. The movable boss 135b is located in a space between the two resilient support pieces 134a and 134b located on the rear side thereof.

That is, the movable boss 135b located on the rear side of the fixing member 135 is moved upward and downward in the space between the two resilient support pieces 134a and 134b while the fixing member 135 is moved upward and downward along the inward hole 131 that is cut away vertically, so that the movable boss 135b restricts the two resilient support pieces 134a and 134b from being shrunk.

As shown in FIGS. 12 and 12a, in a description of an operation, if the fixing member 135 of the connecting member 130 is raised, the movable boss 135b between the two resilient support pieces 134a and 134b is moved upward.

Then, as the movable boss 135b is raised, a space for widening the two resilient support pieces is secured, and if the connecting member 135 is lowered, the two resilient support pieces 134a and 134b are shrunk inward due to a tension by a screw thread and the bosses 134c and 134d, and the movable piece 134 can be moved downward.

Thereafter, if the fixing member 135 is lowered, the movable boss 135b located high is lowered so that the bosses 134c and 134d formed on the outer side cannot be withdrawn to the outside of the screw thread while the two resilient support pieces 134a and 134b are restricted from being shrunk, so that the connecting member 130 can be prevented from being lowered further.

Thus, according to the present invention, since the fixing device 100 can adjust a vertical location of the automatic clamp, more potential energy can be secured. Further, a plurality of automatic clamps can be installed in the linger member.

As shown in FIG. 13, the automatic clamp may further include a relay terminal 200 and a management server 210.

The automatic clamp further includes a wireless communication module to transmit identification information and event information to the outside, and in particular, when an amount of dropping medicine is changed, the automatic clamp generates event information, forms a channel with a searched relay terminal 200 at a periphery thereof, and transmits the event information to the management server 210.

First, the relay terminal 200 is installed at a point that is a branch point of wards or passages to form a sensor network, and transmits identification information and event information to the management server. Then, the relay terminal 200 transmits and reports location information informing of a location thereof together with the identification information.

The management server 210 manages identification information of the automatic clamp allocated to the patients and unique information of the patients in a database, and in particular, it is managed which relay terminals 200 are installed in rooms in a database.

Thus, the management server 210 can identify locations of patients and medicine injection states of the patients based on transmission location information and identification information of the automatic clamp from the relay terminal.

Figure 14:
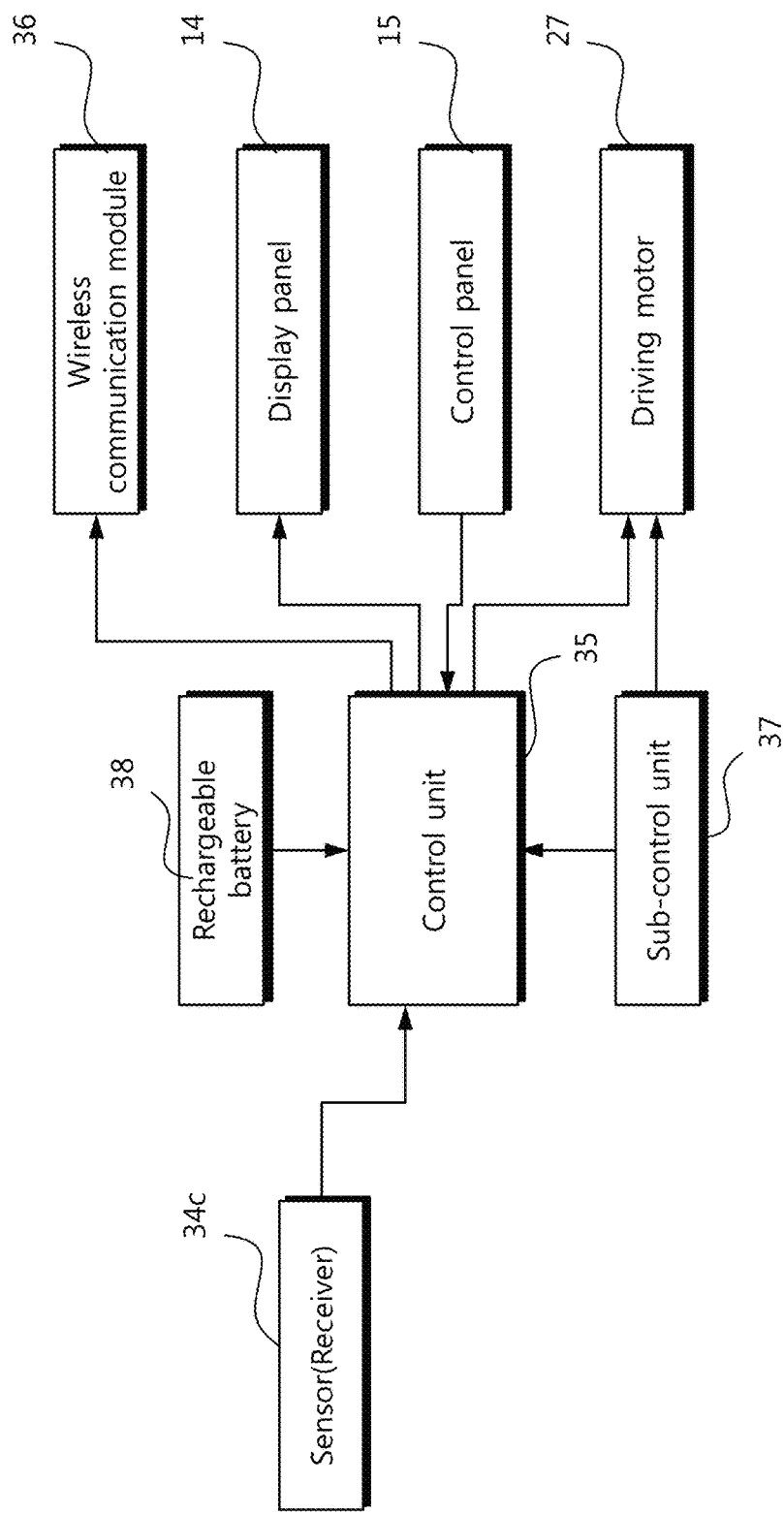
FIG. 14 is a block diagram of the automatic clamp according to the embodiment of the present invention.

As shown in FIG. 14, the automatic clamp includes a detection unit, a control unit, a rechargeable battery, a driving motor, a display panel, and a control panel in the second box or the first box.

First, a cutaway recess 34a is formed in one of the first accommodating part 12 and the second accommodating part 22 and another cutaway recess 34b is formed in the other of the first accommodating part 12 and the second accommodating part 22, and the detection unit 34 is configured such that a pair of embedded sensors 34c detects a movement of a medicine dropping across the cutaway recesses 34a and 34b. The detection unit reports the detected fact to the control unit, and the sensor 34c is not limited to an optical sensor, an infrared ray sensor, an ultrasonic sensor, or a laser sensor, and may include various sensors including a transmitter and a receiver.

The control unit 35 counts the number of drops based on the fact transferred through the detection unit, and calculates an amount of injected medicine or fluid based on the counts to display the amount of medicine or fluid on a display panel.

Then, the control unit 35 counts the number of drops for a set time and compares the amount of previously injected medicine with the amount of currently injected medicine, and controls the driving motor to adjust the amount of dropping medicine if the compared amounts are different.

That is, the controller 35 performs a control to continuously inject a constant amount of medicine even when a pressure of the medicine is changed over time.

Although the display panel 14 and the control panel 15 may be formed in the second box 20, the display panel 14 and the control panel 15 may be formed in the first box 10 and a control board and a flexible board may be connected to the second box while the first box 10 and the second box 20 are foled.

Then, a connecting portion 21g having an inward recess at an end of the side surface 21 of the second box 20, and a cutaway portion 21f at an upper end of the connecting portion are formed the flexible board. A connecting portion and a cutaway portion are formed on the side surface of the first box such that the flexible board of the second box exits out of the cutaway portion and enters the first box to be connected to the sub-control board when a hinge shaft is installed.

The control panel 15 includes a plurality of buttons, and includes a power button for performing an off/off operation, an up/down button for adjusting an amount of injected medicine according to a pressed time, and a setting button.

A rechargeable battery is provided in the first box 10 and the second box 20, and an interface connected to a charging cable or a data cable is formed outside the second box 20.

The present invention may further include a sub-control unit or a wireless communication module within the first box or the second box according to an embodiment.

The sub-control unit 37 identify whether the driving motor is operated as set while monitoring an operation of the control unit. According to an embodiment, when the number of counts detected by the detection unit and the set number do not coincide with each other, the sub-control unit 37 generates a calibration value corresponding to the difference, reports the calibration value to the control unit 35, and rotates the driving motor to adjust an amount of dropping medicine.

The wireless communication module 36 searches a peripheral relay terminal according to an instruction of the control unit, and transmits event information to the verified channel after a verification procedure if a channel with the relay terminal is requested.

The wireless communication module 36 may be variously modified according to an embodiment, but is basically a low power consumption Zigbee communication module that transmits event information at a speed of 250 kbps within 10 to 20 meters based on IEEE 802.15.4.

The wireless communication module is inserted into the box, but a modulized terminal may be inserted into an interface to transmit event information to the outside according to an embodiment.

Figure 15:
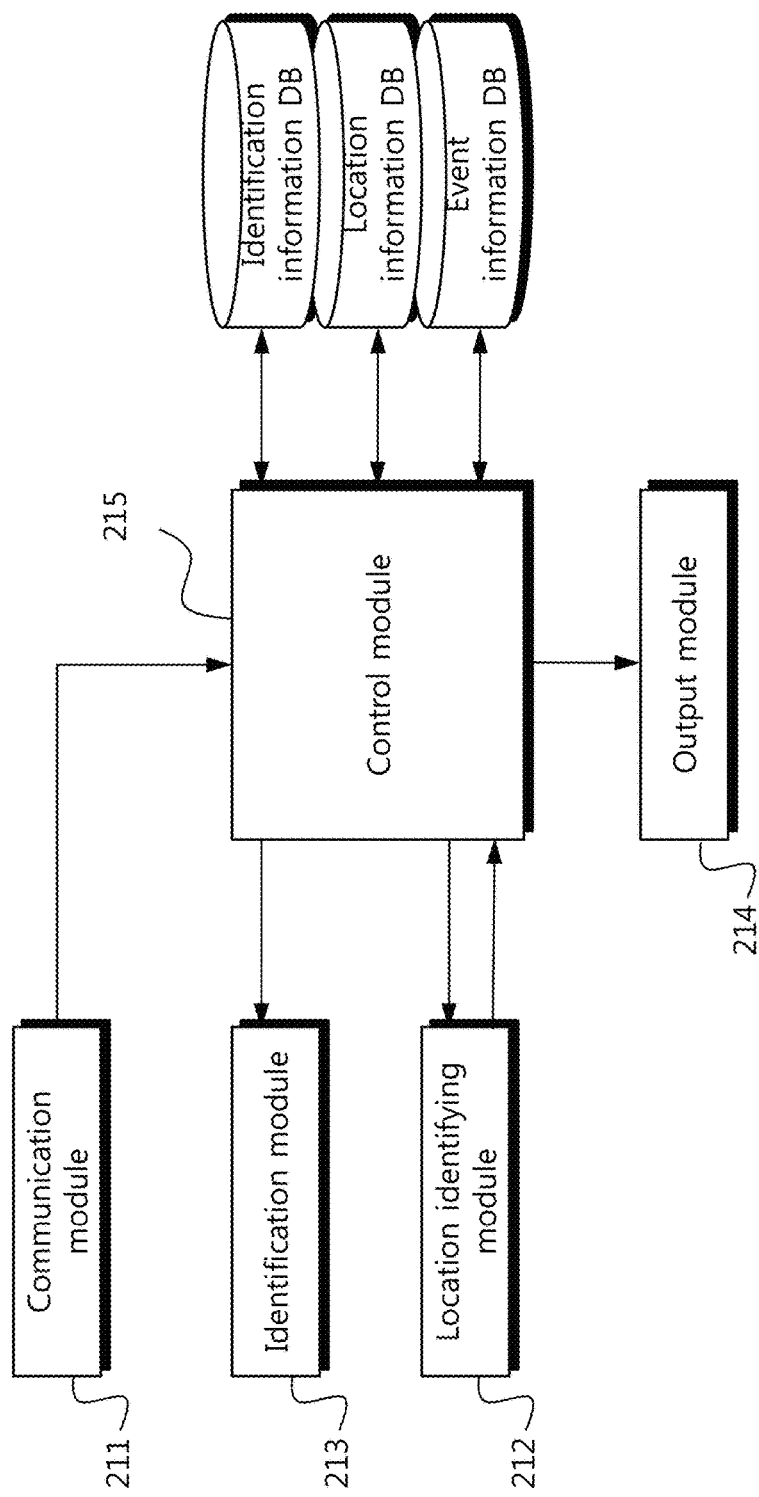
FIG. 15 is a block diagram of a management server according to the embodiment of the present invention.
Figure 16:
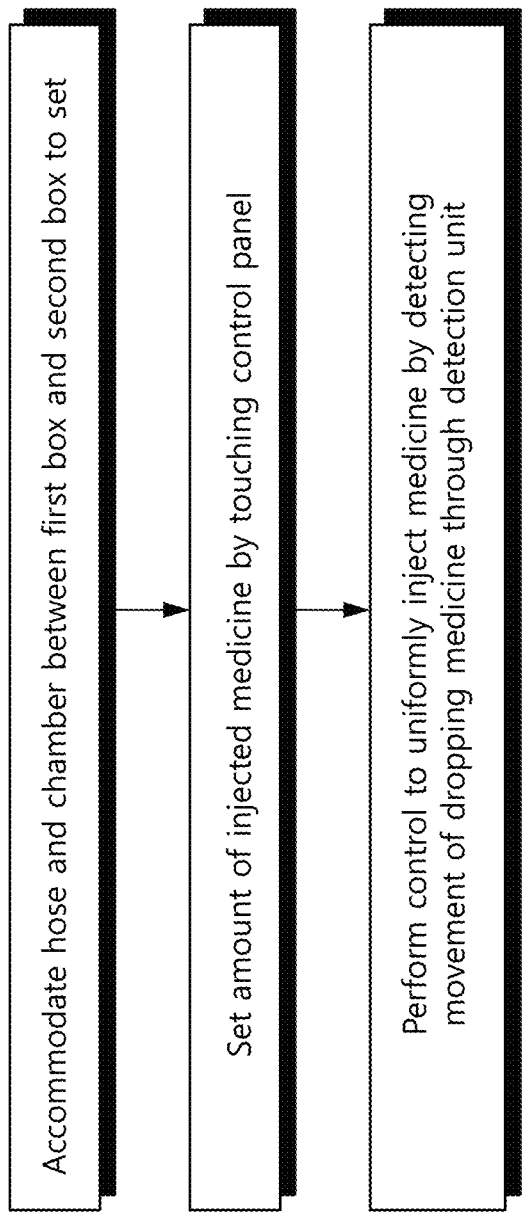
FIG. 16 is a flowchart of the automatic clamp according to the embodiment of the present invention.

As shown in FIG. 15, the management server 210 includes a communication module 211, a location identifying module 212, an identification module 213, an output module 214, and a control module 215 based on information in a database. The modules refer to functional and structural combination of hardware and software for performing the technical spirit of the present invention.

Here, if a communication unit identifies a connection request of the automatic clamp, the communication module 211 receives identification information and location information of the automatic clamp from the relay terminal 200 to report the information to the control module, identifies by whom and from where the identification information is transmitted, and receives event information from the automatic clamp to which a connection is requested.

The location identifying module 212 identifies a location of the relay terminal having transmitted the identification information of the automatic clamp based on a location information database according to an instruction of the control module.

The identification module identifies an automatic clamp of which patient will transmits event information based on a identification information database according to an instruction of the control module.

If receiving identification information and location information through the communication module, the control module 215 make an instruction to identify the transferred identification information and location information through the location identifying module and the identification module. If unique information and a location of the patient are identified, it is request to transmitted event information, and it is instructed to display the event information on a display device through the output module 214.

The control module 215 secures the transmitted event information to store the information in a database, and displays event information on the display device.

The output module 214 displays unique information and a location of a patient according to a platform, and displays the received event information to one side.

Thus, the present invention can manage a state of a medicine injected into a patient, and in particular, even when a patient in a ward moves to another area, can identify the fact, generates a control instruction, and transmits the control instruction to the automatic clamp to interrupt an amount of injected medicine.

Figure 17:
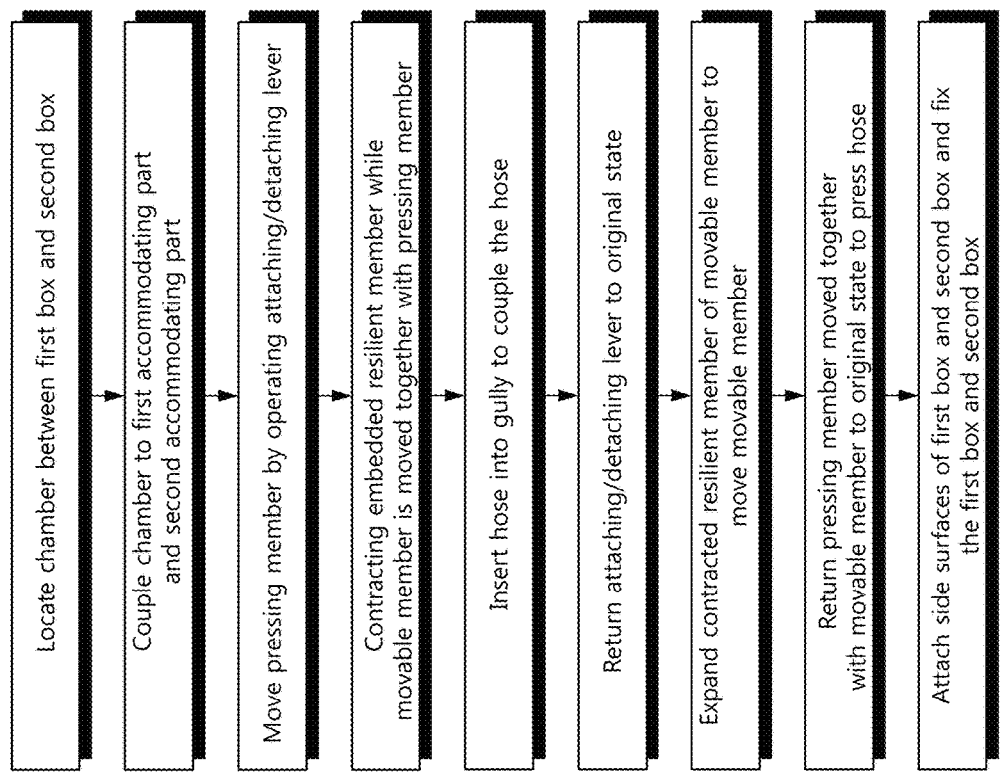
FIGS. 17 and 17A are a flowchart of the automatic clamp according to the embodiment of the present invention.
Figure 17A:
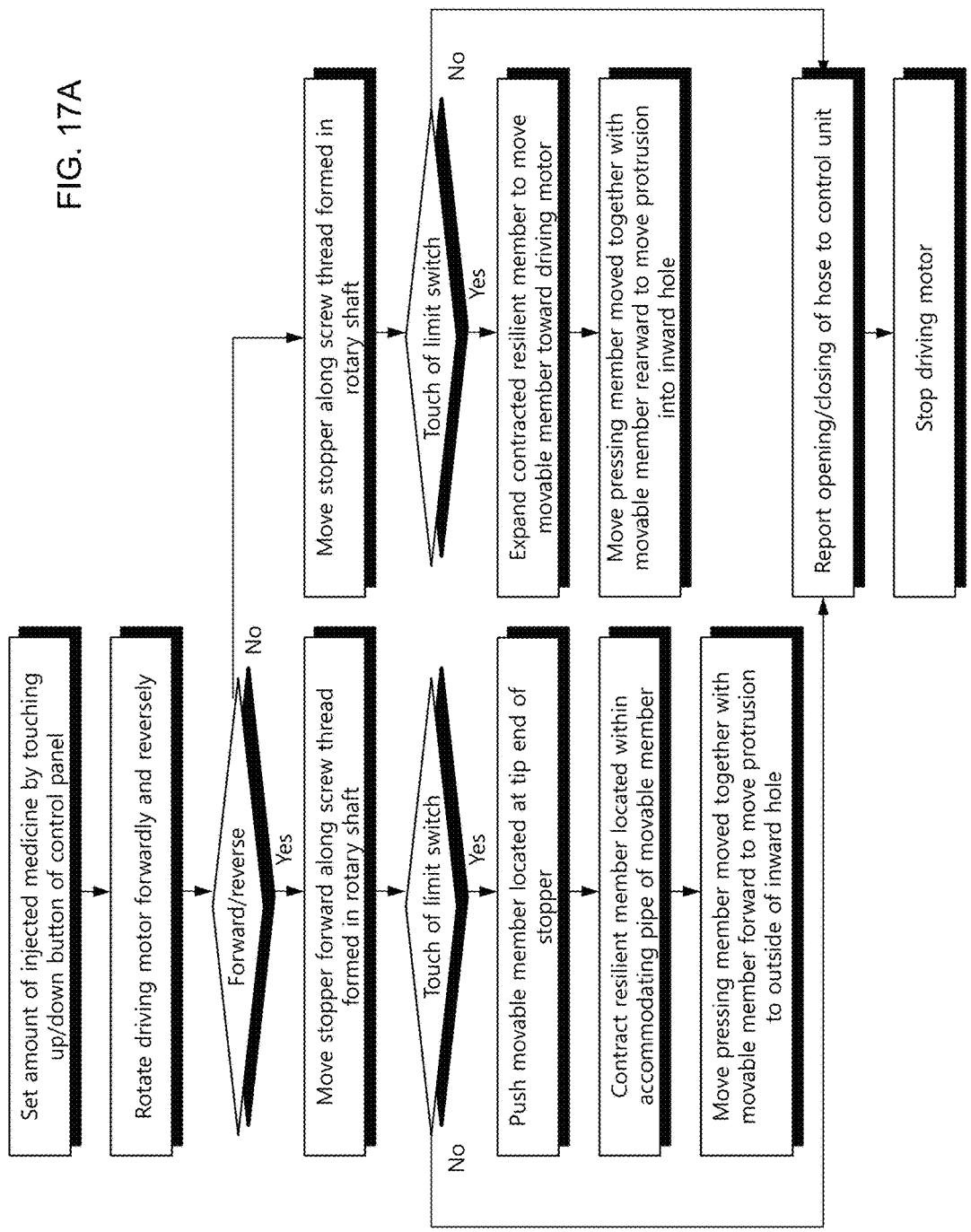

In FIGS. 17 and 17A, an installation process of the automatic clamp according to the embodiment of the present invention will be described with reference to FIG. 6.

First, the locking device is released while a fluid and the hose 2 is installed in the linger member, and the chamber 1 of the hose 2 is located within the first accommodating part 12 and the second accommodating part 22 while the first box 10 and the second box 20 are unfolded.

A lower portion of the chamber 1 is exposed to the insides of the first accommodating part 12 and the second accommodating part 22 while an upper end of the chamber 1 is enclosed by the first connecting part 13 and the second connecting part 23.

Then, if the attaching/detaching lever 29 formed on the side surface 21 of the second box is rotated, the pressing member 31 in the positioning recess 21c is moved so that the protrusion 31a outside the inward hole 21b is moved inward.

For reference, the movable member 28 located at a lower portion of the pressing member 31 is moved together, and the resilient member 33c embedded in the accommodating pipe 28c is contracted.

If the hose 2 of the chamber is inserted into the gulley 21a and the attaching/detaching lever 29 returns to an original state, the resilient member 33c contacted inside the movable member 28 starts to be expanded and the movable member returns to its original state.

Then, the pressing member 31 is moved together with the movable member 28 to move the protrusion 31a to the outside so that the hose 2 inserted into to the gully can be pressed.

Then, the hose i2 is maintained in a state in which a flow of the fluid is normally stopped by preventing the medicine or fluid from being leaked while the hose 2 is pressed by the pressing member 31.

Thereafter, the side surfaces 11 and 21 of the first box 10 and the second box 20 that are unfolded are attached to each other to be fixed by a locking device. Accordingly, the setting is completed.

Thereafter, if a power button of the control panel formed in the first box 10 is pressed, the number of medicine or fluid drops and the injection time are displayed on the display panel 14 while the first box 10 is operated in a basic mode.

Thereafter, if an amount of medicine dropping when the user presses an up button formed on the control panel is set, the driving motor 27 connected to the pressing member 31 is rotated so that the stopper 32 is moved forward and rearward along a screw thread formed in the rotary shaft and the movable member 28 attached thereto is pushed.

Then, the resilient member 33c within the accommodating pipe 28c of the movable member 28 is contracted and the pressing member 31 formed at an upper portion of the movable member 28 is moved together with the movable member 28 so that the hose can be gradually opened while the protrusion 31a of the pressing member 31 is moved inward.

Then, if the driving motor 27 continues to be rotated, the stopping piece 32c of the stopper 32 touches a limit switch 32d and informs the control unit that the hose is fully opened.

Then, if the user presses a down button formed on the control panel to adjust an amount of dropping medicine, the driving motor 27 is rotated reversely, in which case the stopper 32 fitted with the rotary shaft of the driving motor 27 is moved along the screw thread of the rotary shaft so that a distance between the driving motor 27 and the stopper 32 becomes closer.

Then, the movable member 28 located at a tip end of the stopper moves the movable member 28 toward the driving motor 27 while the resilient member 33c contracted in the accommodating pipe 28c is expanded, and if the protrusion 31a of the pressing member 31 appears inside and outside the inward hole 21c while the pressing member 31 formed at an upper portion of the movable member 28 is moved together with the movable member 28, the hose is pressed to adjust an amount of dropping medicine.

Figure 18:
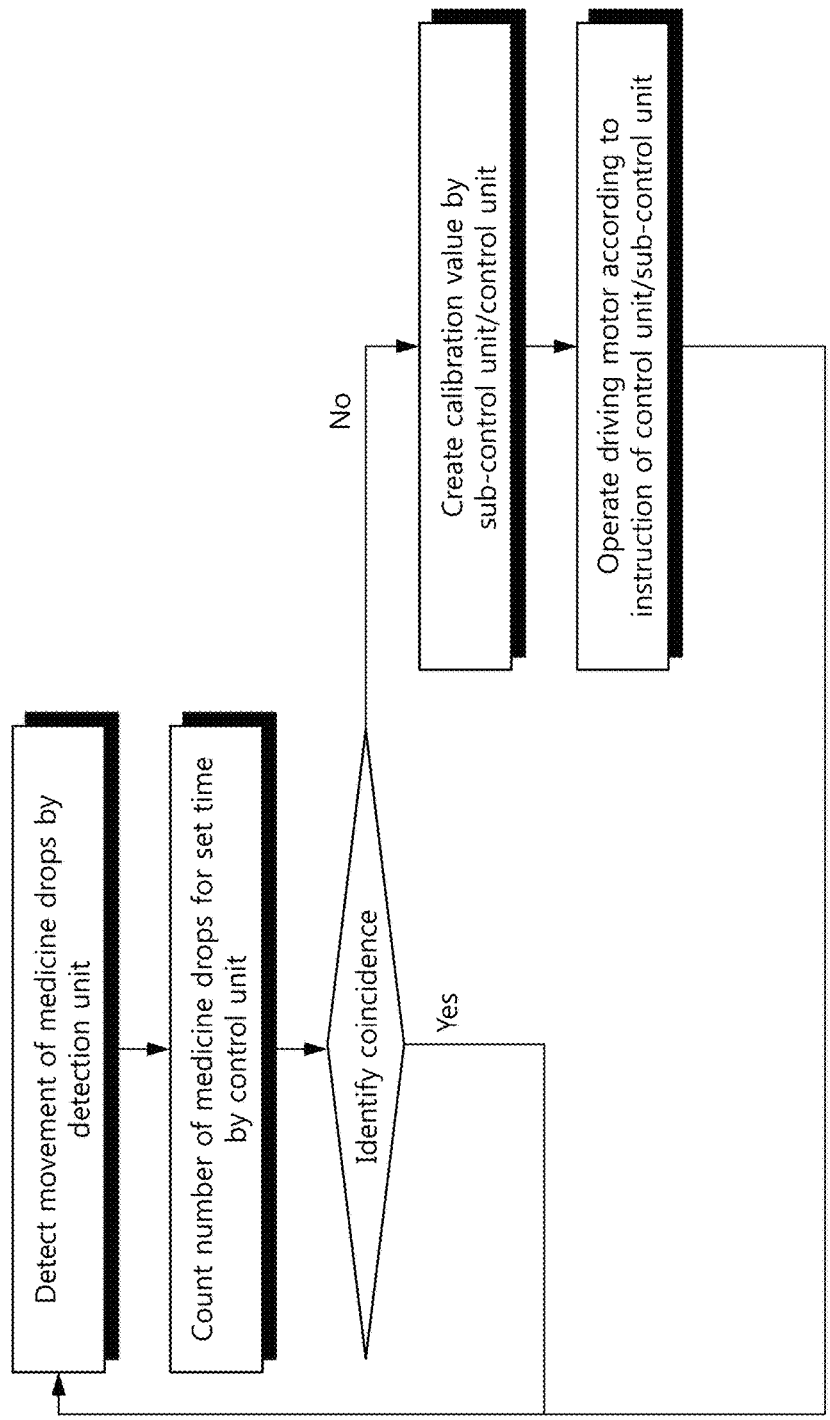
FIG. 18 is a flowchart of the automatic clamp according to the embodiment of the present invention.

If the completely set medicine injector supplies a medicine to a patient, as shown in FIG. 18, the detection unit detects a movement of medicine drops through the sensor installed in the cutaway recesses of the first accommodating part 12 and the second accommodating part 22 and reports the detected fact to the control unit 35.

Then, the control unit counts an amount of medicine dropping for a set time through the detection unit. The control unit identifies whether the number of drops of medicine or fluid for a set time coincides with a set value.

Then, if the results are the same, the control unit repeatedly performs the operation.

However, if the results are not the same, the control unit or the sub-control unit generates a calibration value, controls the driving motor to adjust a location of the pressing member pressing the hose so that the numbers of medicine drops are the same.

Thus, the present invention can continuously inject a constant amount of medicine or fluid even if a pressure of the medicine or fluid decreases over time.

Further, the present invention can adjust a height by using a fixing device.

Figure 19:
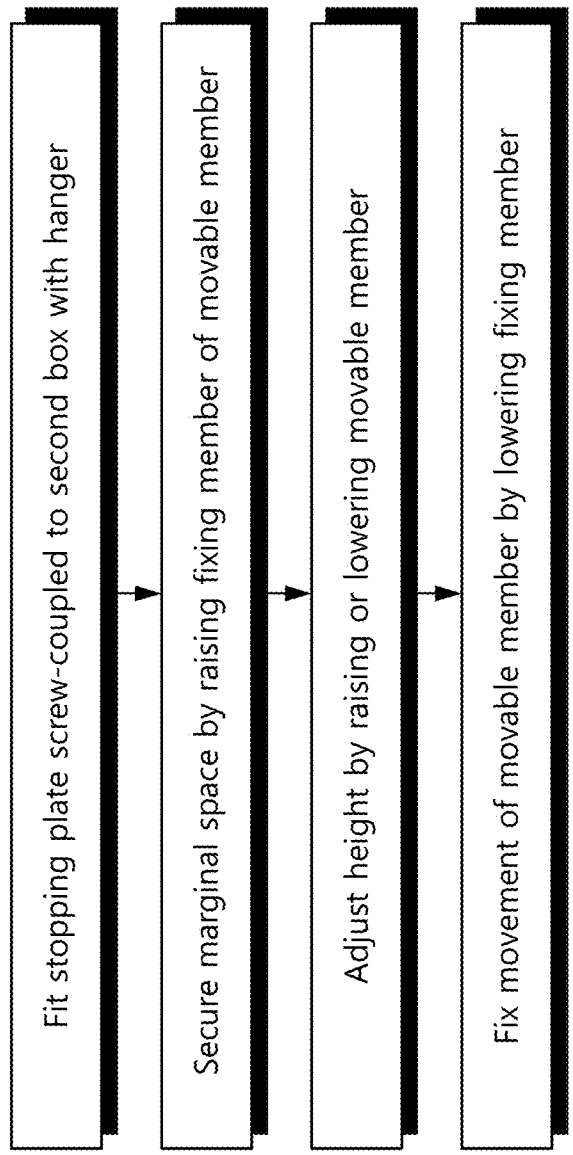
FIG. 19 is a flowchart of the system according to the embodiment of the present invention.

That is, as shown in FIG. 19, a protrusion of the hanger is inserted into and laid on the stopping plate assembled in the second box by using a screw, and the fixing member of the movable member is raised.

Then, as the fixing member is raised, the movable boss formed on a rear surface of the fixing member is also raised. The movable boss between the two resilient support pieces raised so that the resilient support pieces secure a space in which the resilient support pieces can be shrunk.

Then, if the movable member coupled in a sliding manner is raised, the two resilient support pieces prevent a tension so that the resilient support pieces are shrunk to be raised.

If the fixing member is lowered, the movable boss is lowered to prevent the two resilient support pieces from being shrunk, so that the movable member can be fixed so as not to be moved further.

Thus, according to the present invention, since the fixing device can adjust a vertical location of the automatic clamp, the automatic clamp can be used while potential energy thereof is varied. Further, a plurality of automatic clamps may be installed, and in particular, a height of the automatic clamp can be adjusted even when a length between the chamber and the linger member is not proper.

Figure 20:
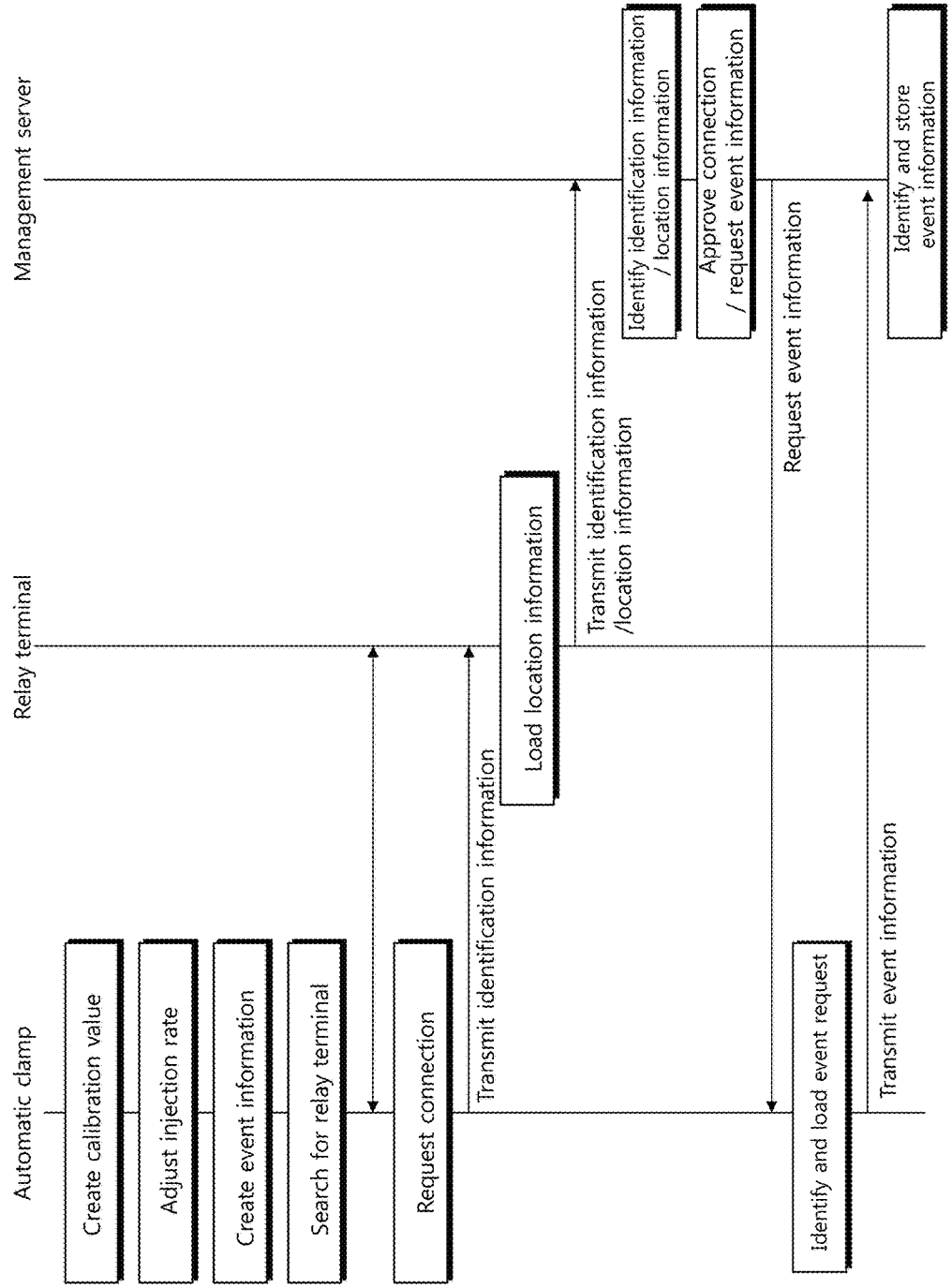
FIGS. 20 and 21 are a flowchart of the system according to the embodiment of the present invention.

As shown in FIG. 20, the present invention transmits event information to a management server located outside to manage the event information according to an embodiment.

That is, if the control unit or the sub-control unit of the automatic clamp generates a calibration value, the control unit or the sub-control unit controls the driving motor.

Then, the control unit generates event information, controls the wireless communication module, and searches for a peripheral relay terminal.

Then, the wireless communication module transmits unique information of the patient or identification information of the automatic clamp, and tries connected to the management server.

Then, the management server identifies identification information of an automatic clamp having requested a connection and location information of a relay terminal having transmitted the identification information, approves a connection, and requests event information of the automatic clamp.

The automatic claim identifies the fact, and transmits the event information to the management server.

The management server identifies the transmitted event information and stores the event information in a database.

Thus, according to the present invention, a state of a medicine injected into a patient can be easily managed at a remote site even when a plurality of automatic clamps are installed.

Figure 21:
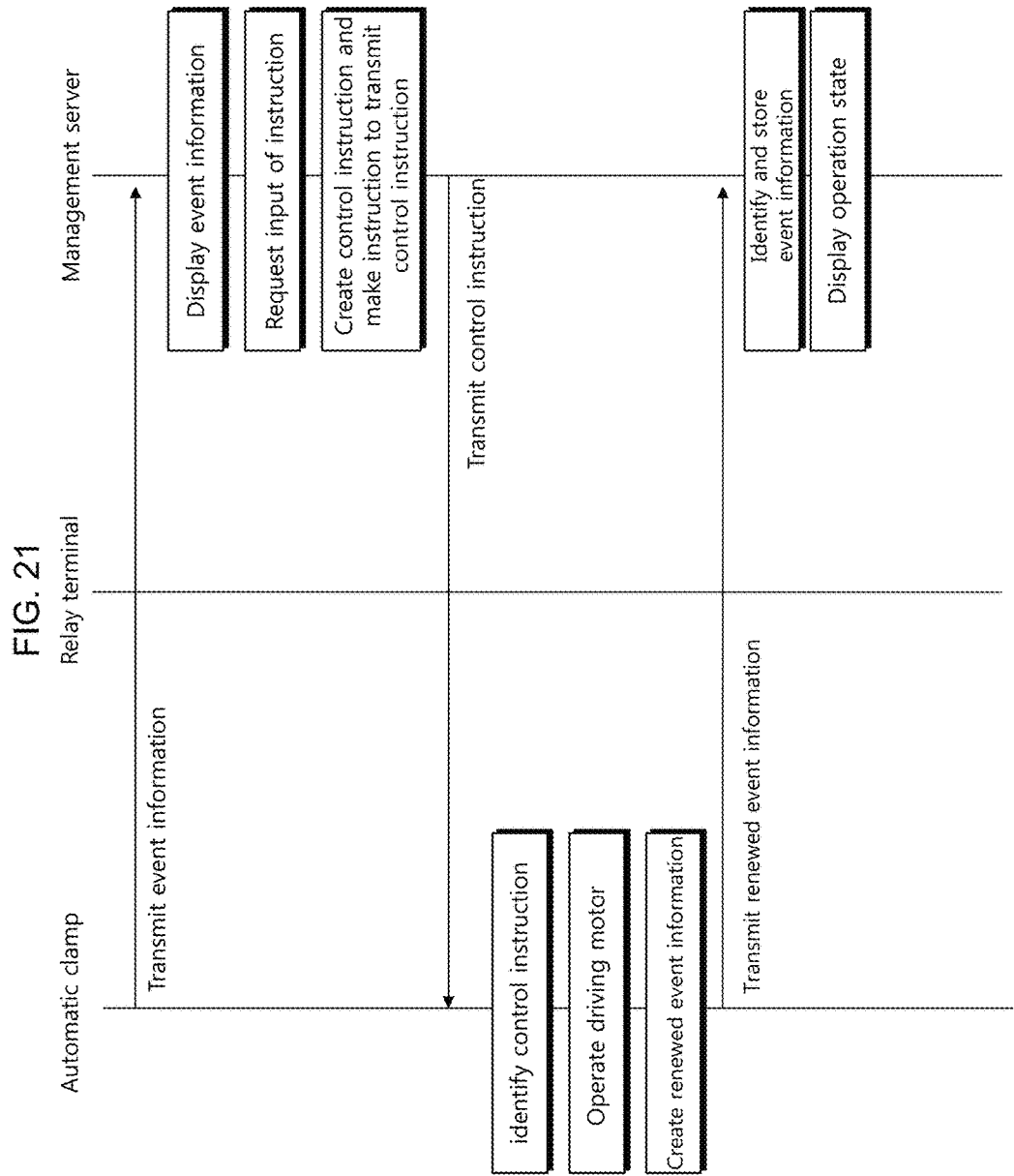

Then, as shown in FIG. 21, the management server receives event information by a preset number of times or more, and if the corresponding automatic clamp identifies that the medicine is not injected as set, the management server displays the fact on the display device and requests an input of an instruction. Then, the displayed event information may be call information for instructing a replacement of a liquid/medicine according to an embodiment.

Thereafter, if an instruction is input according to manipulation of a button, the management server generates a control instruction for controlling the automatic clamp and transmits the control instruction to the automatic clamp.

The automatic clamp identifies the received control instruction, and the control unit makes an instruction to rotate the driving motor and change an amount of dropping medicine.

Thus, the present invention can identify states of a plurality of automatic clamps, and interrupts the automatic clamp so that the medicine/fluid can be injected while the automatic clamp is precisely set even when the automatic clamps are installed in several rooms.

For reference, the automatic clamp can identify the number of medicine drops for a set time to generate event information, and report the fact to the management server to identify whether the automatic claim is operated normally or abnormally.

The invention claimed is:

1. An apparatus for adjusting injection rate through falling, comprising:
   a first box having a first accommodating part extending from one side toward an opposite side thereof;
   a second box having a second accommodating part extending together with the first accommodating part to accommodate a chamber are hinge-coupled to each other such that one side surface of the first box and one side surface of the second box face each other when the first box and the second box are folded;
   an inwardly curved gully into which a hose is inserted when a chamber is accommodated is formed on one of the side surfaces of the first box and the second box;
   a driving unit for controlling a speed of a medicine dropping into the chamber by pressing an outer circumference of a hose inserted into the gully;
   a detection unit for detecting a movement of a medicine dropping into the chamber accommodated in the first accommodating part and the second accommodating part;
   a control unit configured to:
      control a speed of a medicine dropping by controlling the driving unit when a button is manipulated or upon detection by the detection unit, and
      display and guide information identified through a display panel;
   a locking unit for fixing the first box and the second box such that one side surface of the first box and one side surface of the second box are attached to each other when the first box and the second box are folded;
   a positioning recess formed on the side surface of the second box, and an inward hole passes through the positioning recess and a gulley;
   a pressing member positioned in the positioning recess, the pressing member is moved to one side as a movable member accommodating a driving motor and a resilient member embedded in the second box is operated so that a protrusion appears inside and outside the inward hole;
   a flat assembly plate formed at an upper portion of the positioning recess,
   a burying part having a cutaway portion formed at a lower portion of the assembly plate, and
   an attaching/detaching lever having a protruding piece that appears inside and outside the cutaway portion, the attaching/detachable lever is coupled to an upper portion of the burying part to be rotated.

2. The apparatus of claim 1, further comprising:
   a first connecting part and a second connecting part extending from the first accommodating part and the second accommodating part to enclose an upper portion of the chamber are formed at upper portions of the first box and the second box, wherein the first connecting part and the second connecting part fix a support step formed by extending upper ends of the side surfaces of the first box and the second box to the outside and cutting cut away the extending upper ends of the side surfaces such that an upper end of the chamber is laid on the support step; and a lower portion of the chamber fixed to the first accommodating part and the second accommodating part to be exposed by forming a through-hole enclosing a periphery of an upper end of the chamber when the first and second boxes are folded.

3. The apparatus of claim 1, wherein the pressing member comprises:
a flat guide plate,
a protrusion formed at one end of the guide plate at a height larger than a thickness of the guide plate,
a guide groove that is cut away transversely, and
a coupling hole extending from an upper side to a lower side thereof, so that the protruding piece of the lever is located inside the guide groove through the cutaway space such that the protrusion in the gulley is moved inward by pulling the pressing member inward.

4. The apparatus of claim 1, further comprising:
a pair of guides protruding leftward and rightward formed in the positioning recess is mounted; and
a space that is cutaway leftward and rightward informed between the adjacent two guides.

5. The apparatus of claim 4, further comprising:
a movable member including a coupling part located in the cutaway space to be connected to the pressing member;
a tubular accommodating pipe formed at left and right sides of the coupling part and the accommodating hole 28b such that one side of the tubular accommodating pipe is blocked;
a protruding pin formed inside the tubular accommodating pipe; and
a cutting line that is cut away leftward and rightward on an outer side of the tubular accommodating pipe, the cutting line is coupled to a pressing member to be moved together with the pressing member.

6. The apparatus of claim 5,
wherein the support piece in which a resilient member is fitted with a boss is inserted into the tubular accommodating pipe of the movable member, and
wherein the apparatus further comprises a step located inside the cutting line to prevent separation of the movable member is formed in the boss and the support piece is inserted into and assembled in the movable member.

7. The apparatus of claim 6, further comprising:
a protruding movable portion is formed at a lower end of the movable member;
a pair of guide grooves spaced apart from each other by a predetermined separation is formed inside the second box, and
a guide fixing piece and a guide stopping piece erected at a high position are formed at opposite ends of the guide groove, so that the movable member can be moved forward and rearward along the guide groove.

8. The apparatus of claim 1, further comprising:
a stopper for reporting an opened or closed state of the medicine hose while linearly reciprocating along a screw thread formed in the rotary shaft of the driving motor is coupled to the driving motor.

9. The apparatus of claim 8,
wherein the stopper includes a pair of wings on left and right surfaces of a circular column of the stopper, and
wherein the apparatus further comprises a protruding stopping piece is formed in one of the wings, so that if the circular column fitted with the rotary shaft of the driving motor is inserted into the accommodating hole of the movable member with a certain clearance, the wings formed on the left and right side surfaces of the circular column are located at a rear end of a tubular accommodating pipe of the movable member to push the movable member to the outside.

10. The apparatus of claim 9, wherein the stopping pieces of the wings are located between a pair of limit switches installed in a control board to limit a movement of the column within a predetermined range, and enable the limit switches to report an opened state of the hose when the limit switches are touched.

11. The apparatus of claim 1, further comprising:
a protruding portion protruding sharply in a direction perpendicular to the hose inserted into the gully is formed in the protrusion of the pressing member.

* * * * *